US007332593B2

(12) United States Patent
Searfoss, III et al.

(10) Patent No.: US 7,332,593 B2
(45) Date of Patent: Feb. 19, 2008

(54) VARIANTS OF TRAF2 WHICH ACT AS AN INHIBITOR OF TNF-ALPHA (TNFα) SIGNALING PATHWAY

(75) Inventors: George H. Searfoss, III, Birdsboro, PA (US); Marco F. Pagnoni, Norristown, PA (US); Yuri D. Ivashchenko, Norristown, PA (US); Kun Guo, Norristown, PA (US); Kenneth L. Clark, Stevenage (GB)

(73) Assignee: sanofi-aventis U.S. LLC, Bridgewater, NJ (US)

( * ) Notice: Subject to any disclaimer, the term of this patent is extended or adjusted under 35 U.S.C. 154(b) by 61 days.

(21) Appl. No.: 11/294,246

(22) Filed: Dec. 5, 2005

(65) Prior Publication Data
US 2007/0015699 A1    Jan. 18, 2007

Related U.S. Application Data

(63) Continuation of application No. 10/018,030, filed as application No. PCT/US00/09178 on Apr. 6, 2000, now Pat. No. 6,998,475.

(60) Provisional application No. 60/131,940, filed on Apr. 30, 1999.

(51) Int. Cl.
C12N 5/10 (2006.01)
C12N 15/12 (2006.01)
C12N 15/63 (2006.01)

(52) U.S. Cl. .................. 536/23.1; 435/320.1; 435/325; 435/252.3; 435/254.11

(58) Field of Classification Search ..................... None
See application file for complete search history.

(56) References Cited

OTHER PUBLICATIONS

Rothe et al., *A Novel Family of Putative Signal Transducers Associated With the Cytoplasmic Domain of the 75 kDa Tumor Necrosis Factor Receptor*, Cell, vol. 78: p. 681-692 (Aug. 26, 1994).
Hsu et al., TRADd-TRAF2 and TRADD-PADD Interactions Define Two Distinct TNF Receptor 1 Signal Transduction Pathways, Cell, vol. 84: p. 299-308 (Jan. 26, 1996).
Rothe et al., *TRAF2—Medicated Activation of NF-$_kB$ by TNF Receptor 2 and CD40*, Science vol. 269: p. 1424-1427 (Sep. 8, 1995).
Lee, et al., *CD30/TNF Receptor-Associated Factor Interaction: NF-$_kB$ Activation and Binding Specificity*, PNAS vol. 93, p. 9699-9703 (Sep. 1996).
Horie et al., *A Novel Domain in the CD30 Cytoplasmic Tail mediates NfkB Activation*, International Immunology vol. 10, No. 2, p. 203-210 (Feb. 2, 1998).
Duckett, et al., *Inducgtion of Nuclear Factor $_kB$ by the CD 30 Receptor is Mediated by TRAF1 and TRAF2*, Mol. and Cell. Biol. vol. 17 No. 3, p. 1535-1542 (Mar. 1997).
Dadgostar et al., *An Intact zinc Ring Finger is Required for tumor Necrosis Factor Receptor-Associated Factor-Mediated Nuclear Factor-$_kB$ Activation But Is Dispensable for c-Jun N-terminal Kinase Signaling*, J. Biol. Chem. vol. 272, No. 38, p. 24775-24780 (Sep. 18, 1998).
Cao et al., *TRAF6 is a Signal Transducer for Interleukin-1*, Nature, vol. 383 p. 443-446 (Oct. 1996).
Brink, et al., *Tumor Necrosis Factor Receptor (TNFR)—associated Factor 2A (TRAF2A), a TRAF2 Splice Variant with an Extended Ring Finger Domain that Inhibits TNFR2-mediated NF-kB Activation*, The Journal of Biological Chemistry, Feb. 13, 1998, vol. 273, No. 7, pp. 4129-4134.
Takeuchi et al., *Distinct Domains for Nuclear Factor-kBActivation and Association with Tumor Necrosis Factor Signaling Proteins*, The Journal of Biological Chemistry, Aug. 16, 1996, vol. 271, No. 33, pp. 19935-19942.
Song, et al., *Tumor Necrosis Factor (TNF)-mediated Kinase Cascades: Bifurcation of Nuclear Factor-kB and c-jun N-terminal Kinase (JNK/SAPK) Pathways at TNF Receptor-associated Factor 2*, Proc. Natl. Acad. Sci., vol. 94, pp. 9792-9796, Sep. 1997, Immunology.
Min, et al., *TNF Initiates E-Selectin Transcription in Human Endothelial Cells Through Parallel TRASF-NF-kB and TRAF-RAC/CDC42-JNK-c-Jun/ATF2 Pathways*, The Journal of Immunology, 1997, vol. 159, pp. 3508-3518.
Bryant, et al., *Cardiac Failure in Transgenic Mice with Myocardial Expression of Tumor Necrosis Factor-a*, Circulatio vol. 97, No. 14, pp. 1375-1381, Apr. 1998.
Kubota, et al., *Dilated Cardiomyopathy in Transgenic Mice with Cardiac-Specific Overexpression of Tumor Necrosis Factor-a*, Circulation Research, vol. 81, No. 4, pp. 627-635, Oct. 1997.
Ursula Muller-Werdan et al., *Cardiodepression by Tumor Necrosis Factor-alpha*, European Cytokine Network, vol. 9, Issue 4, pp. 689-692, Dec. 1998.
Aukrust, et al., *Cytokine Network in Congestive Heart Failure Secondary to Ischemic or Idiopathic Dilated Cardiomyopathy*, The American Journal of Cardiology, vol. 83, No. 3, pp. 376-382, 1999.
Palermo et al., *Transgenic Remodeling of the Contractile Apparatus in the Mammalian Heart*, Circulation Research, vol. 78, No. 3, pp. 504-509, Mar. 1996.
Shani, Moshe, *Tissue-specific expression of rat myosin light-chain 2 gene in transgenic mice*, Nature, vol. 314, No. 21, pp. 283-286, Mar. 1985.
Jeyaseelan, et al., *A Novel Cardiac-Restricted Target for Doxorubicin: Carp, A Nuclear Modulator of Gene Expression in Cardiac Progenitor Cells and Cardiomyocytes*, The Journal of Biological Chemistry, vol. 272, No. 36, pp. 22800-22808, Sep. 5, 1997.

*Primary Examiner*—Prema Mertz
(74) *Attorney, Agent, or Firm*—Synnestvedt & Lechner LLP

(57) ABSTRACT

The present invention relates to variants of TRAF2 which demonstrate the ability to inhibit the TNF α signaling pathway. In particular, applicants have isolated a splice variant of TRAF2 referred to hereinafter as "TRAF2 truncated" or "TRAF2TR" and a TRAF2 expression construct with enhanced dominant negative properties, hereafter referred to as "TRAF2 truncated-deleted" or "TRAF2TD". Both TRAF2TR and TRAF2TD have the ability to inhibit the TNF α signaling pathway and in TRAF2TD, this ability is greatly enhanced, greatly reducing the response to TNF α binding.

4 Claims, 13 Drawing Sheets

```
1   ATGGCTGCAGCTAGCGTGACCCCCCCCTGGCTCCCCTGGAGTTGCTACAGCCCGGCTTCTCCAAGACCCTCCTGGGGACCAA
    GCTGGAAGCCAAGTACCTGTGCTCCGCCCTGCAGAAACGTCCTCCGCAGGCCCTTCCAGGGCGCAGTGTGTGGCCACCGGTACT
    GCTCCTTCTGCCTGGCCAGCATCCTCAGCTCTGGGCCTCAGAACTGTGCTGCCTGTGTTCACGAGGGCATATATGAAGAA
    GGCATTTCTATTTTAGAAAGCAGTTCGGCCCTTCCCAGATAATGCTGCCCGGAGGAGGTGGAGAGAGCCTGCCGGCCGTCTG
    TCCCAGTGATGGATGCACCTGGAAGGGGACCCTGAAAGAATACGAGTTTCAGGACCACGTCAAGACTTGTGGCAAGTGTC
    GAGTCCCTTGCAGATTCCACGCCCATCGGCTGCCTCGAGACGCGGTGAGAGGGTGAGAAACAGCAGGAGCACGAGGTGCAGTGG
    CTGCGGGAGCACCTGGCCATGCTACTGAGCTCGGTGTGCTGGAGGCAAAGCCCCTCTTGGGAGACCCAGAGACCACGCGGGTC
    AGAGCTCCTGCAGAGGTGCGAGAGCCTGGAGAAGAAGACGGCCACACTTTTGAGAACATTGTCTGCGTCCTGAACCGGGAGG
    TGGAGAGGGTGTGGCCATGACTGCCGAGAGCCTGCAGCCGGCTGGACCAGCCAAGACAAGATTGAAGCCCTGAGTAGC
    AAGGTGCAGCAGCTGGAGAGGAGCATTGCCCTCAAGGACCTGGCGATGCTGACTTGGAGCAGAAGGTCTTGGAGATGGA
    GGCATCCACCTACGATGGGGTCTTCATCGAAGATCTCAGACTTcgCCAGGAAGCTCCAGGAAGCTGTGGCTGGCCGCA
    TACCCGCCATCTTCTCCCCAGCCTTCTACACCCAGCAGGTACGGCTACAAGATGTCTGCTATCTACCTGAACGGCGAC
    GGCACCGGGCGAGGAACACACCTGTCCCTCTTCTTTGTGGTGATGAAGGCCCGAATGACGCCCTGCTGCGGTGGCCCTT
    CAACCAGAAGGTGACCTTAATGCTGCTCGACCAGAATAACCGGGAGCACGTGATTGACGTGATTGACGCCCTTCAGCCCGACGTGACTT
    CATCCTCTCTTTCAGAGGCCAGTGCGGGACGATGCCATCTTCATCAAGGCCATTGTGACCTGAGACCTGACAGGGCTCTAA  1269
    GCAAAGAATTCCTACGTGCGGGACGATGCCATCTTCATCAAGGCCATTGTGACCTGAGACCTGACAGGGCTCTAA
```

FIGURE 2a

1 MAAASVTPPGSLELLQPGFSKTLLGTKLEAKYLCSACRNVLRRPFQAQCGHRYCSFCLASILSSGPQNCAACVHEGIYEE
GISILESSSAFPDNAARREVESLPAVCPSDGCTWKGTLKEYEFQDHVKTCGKCRVPCRFHAIGCLETVEGEKQQEHEVQW
LREHLAMLLSSVLEAKPLLGDQSHAGSELLQRCESLEKKTATFENIVCVLNREVERVAMTAEACSRQHRLDQDKIEALSS
KVQQLERSIGLKDLAMADLEQKVLEMEASTYDGVFIWKISDFARKLQEAVAGRIPAIFSPAFYTSRYGYKMCLRIYLNGD
GTGRGTHLSLFFVVMKGPNDALLRWPFNQKVTLMLLDQNNREHVIDAFRPDVTSSSFQRPVNDMNIASGCPLFCPVSKME
AKNSYVRDDAIFIKAIVDLTGL 422

FIGURE 2b

```
ATGAGTTCGGCCTTCCCAGATAATGCTGCCCGCAGGGAGGTGGAGAGCCTGCCCGGCCGTCTG
TCCCAGTGATGATGCACCTGGAAGGGACCCTGAAAGAATACGAGTTTCAGGACCAGTCAAGACTTGTGGCAAGTGTC
GAGTCCCTGCAGATTCCACGCCATCGGCTGCCTCGAGACGGGTAGAGGGTGAGAAACAGCAGGAGCACGAGGTGCAGTGG
CTGCGGGAGCACCTGGCCATGCTACTGAGCTCGGTCGTGCTGGAGGCAAAGCCCCTCTTGGGAGACCAGAGCCACGCGGGGTC
AGAGCTCCTGCAGAGGTGCGAGAGCCTGGAGAGAAGACGGGCCACTTTGAGAACATTGTCTGCTCCTGAACCGGGAGG
TGGAGAGGGTGGCCATGACTGCCGAGGCCTGCAGCCCGGCAGCACCGGCTGACCAAGACAAGATTGAAGCCCTGAGTAGC
AAGGTCAGCAGCTGGAGAGAGCATTGGCCTCAAGGACCTGGCGATGGCTGACTTGGAGCAGAAGGTCTTGGAGATGGA
GGCATCCACCTACGATGGGGTTCTTCATCTCGGAAGATCTCAGACTTCgCCAGGAAGCtCCAGGAAGCTGTGGCCGCA
TACCCGCCATCTTCTCCCCAGCCCTTCTACACCAGCCTTCTCTTTGTGTCGCGTATCTACCTGAACGGGAC
GGCACCGGGCGAGGAACACACCCTGTCCCCTCTTCTTTGTGTGATGAAGGGCCCGAATGACGCCCCTGCTGCGGTGCCCTT
CAACCAGAAGTGACCTTAATGCTGCTGACCAGAATAACCGGGAGCACGTGATTGACGCCTTCAGGCCCGACGTGACTT
CATCCCTCTTTCAGAGGCCAGTCAACGACATGAACATCGCAAGCGGCCTGCCCCCCTCTTCTGCCCCGTCCCAAGATGAG
GCAAAGAATTCCTACGTGCGGGACGATGCCATTCATCAAGGCCATTGTGGACCTGACAGGGCTCTAA
```

FIGURE 3a

MSSAFPDNAARREVESLPAVCPSDGCTWKGTLKEYEFQDHVKTCGKCRVPCRFHAIGCLETVEGEKQQEHEVQW
LREHLAMLLSSVLEAKPLLGDQSHAGSELLQRCESLEKKTATFENIVCVLNREVERVAMTAEACSRQHRLDQDKIEALSS
KVQQLERSIGLKDLAMADLEQKVLEMEASTYDGVFIWKISDFARKLQEAVAGRIPAIFSPAFYTSRYGYKMCLRIYLNGD
GTGRGTHLSLFFVVMKGPNDALLRWPFNQKVTLMLLDQNNREHVIDAFRPDVTSSSFQRPVNDMNIASGCPLFCPVSKME
AKNSYVRDDAIFIKAIVDLTGL

```
              1                                                              50
TRAF2-TR    GAATTCCGGC GCGCTGCGAC CGTTGGGGCT TTGTTCGCGG GGGTCACAGC
TRAF2-FL    GAATTCCGGC GCGCTGCGAC CGTTGGGGCT TTGTTCGCGG GGGTCACAGC 51                                                             100
TRAF2-TR    TCTCATGGCT GCAGCTAGCG TGACCCCCCC TGGCTCCCTG GAGTTGCTAC
TRAF2-FL    TCTCATGGCT GCAGCTAGCG TGACCCCCCC TGGCTCCCTG GAGTTGCTAC 101                                                            150
TRAF2-TR    AGCCCGGCTT CTCCAAGACC CTCCTGGGGA CCAAGCTGGA AGCCAAGTAC
TRAF2-FL    AGCCCGGCTT CTCCAAGACC CTCCTGGGGA CCAAGCTGGA AGCCAAGTAC 151                                                            200
TRAF2-TR    CTGTGCTCCG CCTGCAGAAA CGTCCTCCGC AGGCCCTTCC AGGCGCAGTG
TRAF2-FL    CTGTGCTCCG CCTGCAGAAA CGTCCTCCGC AGGCCCTTCC AGGCGCAGTG 201                                                            250
TRAF2-TR    TGGCCACCGG TACTGCTCCT TCTGCCTGGC CAGCATCCTC AGCTCTGGGC
TRAF2-FL    TGGCCACCGG TACTGCTCCT TCTGCCTGGC CAGCATCCTC AGCTCTGGGC 251                                                            300
TRAF2-TR    CTCAGAACTG TGCTGCCTGT GTTCACGAGG GCATATATGA AGAAGGCATT
TRAF2-FL    CTCAGAACTG TGCTGCCTGT GTTCACGAGG GCATATATGA AGAAGGCATT 301                                                            350
TRAF2-TR    TCTATTTTAG AAAGCAGTTC GGCCTTCCCA GATAATGCTG CCCGCAGGGA
TRAF2-FL    TCTATTTTAG AAAGCAGTTC GGCCTTCCCA GATAATGCTG CCCGCAGGGA 351                                                            400
TRAF2-TR    GGTGGAGAGC CTGCCGGCCG TCTGTCCCAG TGATGGATGC ACCTGGAAGG
TRAF2-FL    GGTGGAGAGC CTGCCGGCCG TCTGTCCCAG TGATGGATGC ACCTGGAAGG 401                                                            450
TRAF2-TR    GGACCCTGAA AGAATACGAG ---------- ---------- ----------
TRAF2-FL    GGACCCTGAA AGAATACGAG AGCTGCCACG AAGGCCGCTG CCCGCTCATG 451                                                            500
TRAF2-TR    ---------- ---------- ---------- ---------- ----------
TRAF2-FL    CTGACCGAAT GTCCCGCGTG TAAAGGCCTG GTCCGCCTTG GTGAAAAGGA 501                                                            550
TRAF2-TR    ---------- ---------- ---------- ---------- ----------
TRAF2-FL    GCGCCACCTG GAGCACGAGT GCCCGGAGAG AAGCCTGAGC TGCCGGCATT
```

FIGURE 4a (continued)

```
             551                                                    600
TRAF2-TR     ---------- ---------- ---------- ---------- ----------
TRAF2-FL     GCCGGGCACC CTGCTGCGGA GCAGACGTGA AGGCGCACCA CGAGGTCTGC 601                                                    650
TRAF2-TR     ---------- ---------- ---------- ---------- ----------
TRAF2-FL     CCCAAGTTCC CCTTAACTTG TGACGGCTGC GGCAAGAAGA AGATCCCCCG 651                                                    700
TRAF2-TR     -------TTT CAGGACCACG TCAAGACTTG TGCAAGTGT CGAGTCCCTT
TRAF2-FL     GGAGAAGTTT CAGGACCACG TCAAGACTTG TGCAAGTGT CGAGTCCCTT 701                                                    750
TRAF2-TR     GCAGATTCCA CGCCATCGGC TGCCTCGAGA CGGTAGAGGG TGAGAAACAG
TRAF2-FL     GCAGATTCCA CGCCATCGGC TGCCTCGAGA CGGTAGAGGG TGAGAAACAG 751                                                    800
TRAF2-TR     CAGGAGCACG AGGTGCAGTG GCTGCGGGAG CACCTGGCCA TGCTACTGAG
TRAF2-FL     CAGGAGCACG AGGTGCAGTG GCTGCGGGAG CACCTGGCCA TGCTACTGAG 801                                                    850
TRAF2-TR     CTCGGTGCTG GAGGCAAAGC CCCTCTTGGG AGACCAGAGC CACGCGGGGT
TRAF2-FL     CTCGGTGCTG GAGGCAAAGC CCCTCTTGGG AGACCAGAGC CACGCGGGGT 851                                                    900
TRAF2-TR     CAGAGCTCCT GCAGAGGTGC GAGAGCCTGG AGAAGAAGAC GGCCACTTTT
TRAF2-FL     CAGAGCTCCT GCAGAGGTGC GAGAGCCTGG AGAAGAAGAC GGCCACTTTT 901                                                    950
TRAF2-TR     GAGAACATTG TCTGCGTCCT GAACCGGGAG GTGGAGAGGG TGGCCATGAC
TRAF2-FL     GAGAACATTG TCTGCGTCCT GAACCGGGAG GTGGAGAGGG TGGCCATGAC 951                                                    1000
TRAF2-TR     TGCCGAGGCC TGCAGCCGGC AGCACCGGCT GGACCAAGAC AAGATTGAAG
TRAF2-FL     TGCCGAGGCC TGCAGCCGGC AGCACCGGCT GGACCAAGAC AAGATTGAAG 1001                                                   1050
TRAF2-TR     CCCTGAGTAG CAAGGTGCAG CAGCTGGAGA GGAGCATTGG CCTCAAGGAC
TRAF2-FL     CCCTGAGTAG CAAGGTGCAG CAGCTGGAGA GGAGCATTGG CCTCAAGGAC 1051                                                   1100
TRAF2-TR     CTGGCGATGG CTGACTTGGA GCAGAAGGTC TTGGAGATGG AGGCATCCAC
TRAF2-FL     CTGGCGATGG CTGACTTGGA GCAGAAGGTC AGGCCCTTCC AGGCGCAGTG
```

FIGURE 4a (continued)

```
              1101                                              1150
TRAF2-TR      CTACGATGGG GTCTTCATCT GGAAGATCTC AGACTTTCCC AGGAAGCTCC
TRAF2-FL      TGGCCACCGG TACTGCTCCT TCTGCCTGGC CAGCATCCTC AGGAAGCTCC 1151                                              1200
TRAF2-TR      AGGAAGCTGT GGCTGGCCGC ATACCCGCCA TCTTCTCCCC AGCCTTCTAC
TRAF2-FL      AGGAAGCTGT GGCTGGCCGC ATACCCGCCA TCTTCTCCCC AGCCTTCTAC 1201                                              1250
TRAF2-TR      ACCAGCAGGT ACGGCTACAA GATGTGTCTG CGTATCTACC TGAACGGCGA
TRAF2-FL      ACCAGCAGGT ACGGCTACAA GATGTGTCTG CGTATCTACC TGAACGGCGA 1251                                              1300
TRAF2-TR      CGGCACCGGG CGAGGAACAC ACCTGTCCCT CTTCTTTGTG GTGATGAAGG
TRAF2-FL      CGGCACCGGG CGAGGAACAC ACCTGTCCCT CTTCTTTGTG GTGATGAAGG 1301                                              1350
TRAF2-TR      GCCCGAATGA CGCCCTGCTG CGGTGGCCCT TCAACCAGAA GGTGACCTTA
TRAF2-FL      GCCCGAATGA CGCCCTGCTG CGGTGGCCCT TCAACCAGAA GGTGACCTTA 1351                                              1400
TRAF2-TR      ATGCTGCTCG ACCAGAATAA CCGGGAGCAC GTGATTGACG CCTTCAGGCC
TRAF2-FL      ATGCTGCTCG ACCAGAATAA CCGGGAGCAC GTGATTGACG CCTTCAGGCC 1401                                              1450
TRAF2-TR      CGACGTGACT TCATCCTCTT TTCAGAGGCC AGTCAACGAC ATGAACATCG
TRAF2-FL      CGACGTGACT TCATCCTCTT TTCAGAGGCC AGTCAACGAC ATGAACATCG 1451                                              1500
TRAF2-TR      CAAGCGGCTG CCCCCTCTTC TGCCCCGTCT CCAAGATGGA GGCAAAGAAT
TRAF2-FL      CAAGCGGCTG CCCCCTCTTC TGCCCCGTCT CCAAGATGGA GGCAAAGAAT 1501                                              1550
TRAF2-TR      TCCTACGTGC GGGACGATGC CATCTTCATC AAGGCCATTG TGGACCTGAC
TRAF2-FL      TCCTACGTGC GGGACGATGC CATCTTCATC AAGGCCATTG TGGACCTGAC 1551                                              1600
TRAF2-TR      AGGGCTCTAA CTGCCCCCTA CTGGTGTCTG GGGGTTGGGG GCAGCCAGGC
TRAF2-FL      AGGGCTCTAA CTGCCCCCTA CTGGTGTCTG GGGGTTGGGG GCAGCCAGGC 1601                                              1650
TRAF2-TR      ACAGCCGGCT CACGGAGGGG CCACCACGCT GGGCCAGGGT CTCACTGTAC
TRAF2-FL      ACAGCCGGCT CACGGAGGGG CCACCACGCT GGGCCAGGGT CTCACTGTAC
```

FIGURE 4a (continued)

```
              1651                                                    1700
TRAF2-TR      AAGTGGGCAG GGGCCCCGCT TGGGCGCTTG GGAGGGTGTC GGCCTGCAGC
TRAF2-FL      AAGTGGGCAG GGGCCCCGCT TGGGCGCTTG GGAGGGTGTC GGCCTGCAGC 1701                                                    1750
TRAF2-TR      CAAGTTCACT GTCACGGGGG AAGGAGCCAC CAGCCAGTCC TCAGATTTCA
TRAF2-FL      CAAGTTCACT GTCACGGGGG AAGGAGCCAC CAGCCAGTCC TCAGATTTCA 1751                                                    1800
TRAF2-TR      GAGACTGCGG AGGGGCTTGG CAGACGGTCT TAGCCAAGGG CTGTGGTGGC
TRAF2-FL      GAGACTGCGG AGGGGCTTGG CAGACGGTCT TAGCCAAGGG CTGTGGTGGC 1801                                                    1850
TRAF2-TR      ATTGGCCGAG GGTCTTCGGG TGCTTCCCAG CACAAGCTGC CCTTGCTGTC
TRAF2-FL      ATTGGCCGAG GGTCTTCGGG TGCTTCCCAG CACAAGCTGC CCTTGCTGTC 1851                                                    1900
TRAF2-TR      CTGTGCAGTG AAGGGAGAGG CCCTGGGTGG GGGACACTCA GAGTGGGAGC
TRAF2-FL      CTGTGCAGTG AAGGGAGAGG CCCTGGGTGG GGGACACTCA GAGTGGGAGC 1901                                                    1950
TRAF2-TR      ACATCCCAGC AGTGCCCATG TAGCAGGAGC ACAGTGGATG GCCTTGTGTC
TRAF2-FL      ACATCCCAGC AGTGCCCATG TAGCAGGAGC ACAGTGGATG GCCTTGTGTC 1951                                                    2000
TRAF2-TR      CCTCGGGCAT GACAGGCAGA AACGAGGGCT GCTCCAGGAG AAGGGCCTCC
TRAF2-FL      CCTCGGGCAT GACAGGCAGA AACGAGGGCT GCTCCAGGAG AAGGGCCTCC 2001                                                    2050
TRAF2-TR      TGCTGGCCAG AGCAAGGAAG GCTGAGCAGC TTGGTTCTCC CCTCTGGCCC
TRAF2-FL      TGCTGGCCAG AGCAAGGAAG GCTGAGCAGC TTGGTTCTCC CCTCTGGCCC 2051                                                    2100
TRAF2-TR      CTGGAGAGAA GGGAGCATTC CTAGACCCCT GGGTGCTTGT CTGCACAGAG
TRAF2-FL      CTGGAGAGAA GGGAGCATTC CTAGACCCCT GGGTGCTTGT CTGCACAGAG 2101                                                    2150
TRAF2-TR      CTCTGGTCTG TGCCACCTTG GCCAGGCTGG CTGTGGGAGG GTCTGGTCCC
TRAF2-FL      CTCTGGTCTG TGCCACCTTG GCCAGGCTGG CTGTGGGAGG GTCTGGTCCC 2151                                                    2200
TRAF2-TR      ACGCCGCCTC TGCTCAGACA CTGTGTGGGA GGGCACAGCA CAGCTGCGGG
TRAF2-FL      ACGCCGCCTC TGCTCAGACA CTGTGTGGGA GGGCACAGCA CAGCTGCGGG
```

FIGURE 4a (continued)

```
          2201                                                      2250
TRAF2-TR  TAAAGTGTGA GAGCTTGCCA TCCAGCTCAC GAAGACAGAG TTATTAAACC
TRAF2-FL  TAAAGTGTGA GAGCTTGCCA TCCAGCTCAC GAAGACAGAG TTATTAAACC 2251       2262
TRAF2-TR  ATTACAAATC TC
TRAF2-FL  ATTACAAATC TC
```

VARIANTS OF TRAF2 WHICH ACT AS AN INHIBITOR OF TNF-ALPHA (TNFα) SIGNALING PATHWAY

CROSS-REFERENCE TO RELATED APPLICATIONS

This application is a continuation of U.S. application Ser. No. 10/018,030, filed Sep. 23, 2002, now U.S. Pat. No. 6,998,475 which is a National Stage application based on International Application No. PCT/US00/09178, filed Apr. 6, 2000, which claims priority to U.S. Provisional Application No. 60/131,940, filed Apr. 30, 1999, the disclosures of which are incorporated herein by reference.

FIELD OF THE INVENTION

Tumor necrosis factor α (TNF α) is an intercellular mediator of immune responses produced by a variety of cells, including activated macrophages and monocytes. The responses triggered by TNF α are initiated through its interaction with two distinct TNF α cell surface receptors: TNFαR1 and TNFαR2. TNF α binds to these cell surface receptors and triggers activation of transcriptional factors, for example, nuclear factor κB (NFκB), which regulate the expression of a variety of immune and inflammatory response genes.

Upon the binding of TNF α, the TNF α receptors interact through their cytoplasmic domains with a variety of intracellular signal translation proteins. One group of intracellular signal translation proteins known to associate with the TNF α receptors are the tumor necrosis factor receptor associated factors known as the "TRAF" family of receptor proteins. The TRAF family is comprised of a number of homologous proteins which share common structural features and which associate with and transduce signals from TNF α receptor proteins. The TRAF proteins lack enzymatic activity motifs and instead appear to function as adapter proteins which couple the receptors to downstream signaling cascades. One member of the family, TRAF2, associates with a number of TNF α receptor family proteins, including TNFαR1, TNFαR2, CD40 and CD30. For TRAF2, direct binding of at least eight intracellular molecules has been identified. TRAF2 has been shown to be critical for TNF α mediated activation of a variety of transcriptional factors, in particular, NFκB and the C-jun N-terminal kinase (JNK/SAPK) and these transcription factors are in turn responsible for expression of an immune/inflammatory response.

There are a variety of disease states that are linked to regulatory pathways controlled by TNF α binding. In some instances, TNF α binding triggers an inflammatory response which ultimately results in a disease state. Accordingly, it would be desirable to develop means for preventing diseases related to TNF α receptor binding. In particular, it would be desirable to find a way to prevent activation of an inflammatory response that would otherwise be initiated by TNF α activation. The present invention provides polypeptides which are based on TRAF2 and which are capable of inhibiting the TNF α signaling pathways in order to treat and prevent diseases linked to TNF α binding.

REPORTED DEVELOPMENTS

The general structure of the TRAF proteins has been described and is illustrated generally in FIG. 1(a) which shows in diagrammatic form full-length TRAF2 (TRAF2-FL). These proteins have an N-terminal region with a zinc ring finger motif, followed by an array of zinc finger-like structures. The zinc finger region is followed by a conserved (TRAF) domain which is composed of two subdomains: an N-terminal domain and a C-terminal domain. The C-terminal domain is involved in receptor association and homo-, as well as hetero-oligomerization of TRAFs, and serves as a docking site for a variety of other signaling proteins.

TRAF2 follows the general structure of the TRAF proteins described above. A number of studies have attempted to correlate the structural subdomains of the TRAF2 protein with the protein's functions.

Takeuchi et al. performed extensive mutational analysis on TRAF2 (Takeuchi et al., *J. Biol. Chem.*, 271(33) 19935-42 (1996)). These studies suggest TRAF2 is composed of modular domains mediating distinct activities. The authors determined that the N-terminal ring finger and 2 adjacent zinc fingers of TRAF2 are required for NFκB activation and that the distinct TRAF-N and TRAF-C subdomains within the TRAF domain appear to independently mediate self association and interaction with TRAF1.

Song et al. (*Proc. Natl. Acad. Sci.* USA, 94, 9792-9796 (1997)) followed up on studies showing that the TNF α induced activation of NFκB and the c-jun N-terminal kinase (JNK/SAPK) requires TRAF2. The authors showed that TRAF2 is the bifurcation point of two kinase cascades leading to activation of NFκB and JNK. This observation supports a functional model for TRAF2 and other members of the TRAF family as adaptor proteins with docking sites for additional signaling proteins that initiate parallel downstream responses.

Min et al. (*J. Immunology*, 159, 3508-3518 (1997)) used a transfection/overexpression strategy to analyze the roles of TRAF proteins. TRAF2 containing the TRAF domain, but lacking amino terminal residues 1-80 had been previously shown to inhibit TNF α induced NFκB activation. The authors demonstrated that this TRAF2 variant also blocked JNK activation by TNF α.

Brink et al., (*J. Biol. Chem.*, 273, 7, 4129-4134 (1998)) described a splice variant of TRAF2 which they called "TRAF2A." The cDNA of TRAF2A is identical to TRAF2 with the exception of an extra 21 bp of sequence encoding a seven amino acid insert within the TRAF2A ring finger domain. The authors found that TRAF2A mRNA expression is regulated in a tissue specific manner and TRAF2A protein is capable of binding to the cytoplasmic domain of TNFαR2. They also found that, in contrast to TRAF2, TRAF2A is unable to stimulate NFκB activity when overexpressed in 293 cells and acts as a dominant inhibitor of TNFαR2 dependent NFκB activation.

Many studies have linked inflammatory processes and TNFα with the major cardiovascular disease states (Bryant et al., *Circulation*, 97(14):1375-81 (1998); Kubota et al., *Circ. Res.*, 81(4):627-35 (1997); Muller Werdan et al., *Eur. Cytokine Netw.*, 9(4):689-91 (1998); Aukrust et al., *Am. J. Cardiol.*, 83(3):376-82 (1999)). Over the past five years, evidence has accumulated which indicates that raised local TNF α levels are associated with: (a) cardiac ischemia-reperfusion injury which follows myocardial infarction, coronary artery bypass surgery, cardiac transplantation or ischemia-reperfusion injury in the CNS following stroke; (b) the progression and rupture of advanced coronary atherosclerotic plaques; (c) the development and progression of congestive-heart failure; and (d) endothelial cell injury following balloon angioplasty. In addition, recent findings suggest that apoptotic cell death may be an important factor in the pathophysiology of myocardial cell death during heart failure or infarction. It is known that TNF α can induce myocyte apoptosis.

In addition to the cardiovascular disease states mentioned above, there are a variety of other disease states whose pathogenesis is linked to TNF α, These disease states include Crohn's disease, psoriasis, rheumatoid arthritis, graft versus host disease, inflammatory bowel disease, non-insulin dependent diabetes and neurodegenerative diseases (e.g., Parkinson's disease).

Given the relationship between TNF α and a large variety of diseases such as those discussed above, it would be desirable to provide compositions and methods for inhibiting and treating these disease states.

SUMMARY OF THE INVENTION

In accordance with the present invention, it has been found that variants of TRAF2, in particular, a variant that includes a naturally occurring splice variation (TRAF2TR) and a variant that includes the naturally occurring splice variation and a deletion in the N-terminal region of TRAF2 (TRAF2TD), provide for inhibition of TNF α signal transduction and the associated immune inflammatory responses.

In accordance with one embodiment of the present invention, there is provided a DNA sequence encoding TRAF2TR comprising the sequence as shown in FIG. 2a.

In accordance with another embodiment of the present invention, there is also provided a DNA sequence encoding TRAF2TD comprising the sequence as shown in FIG. 3a.

In a preferred embodiment, the TRAF2TR and TRAF2TD DNA are cDNAs.

In other embodiments, the present invention provides a TRAF2TR polypeptide which is capable of inhibiting tumor necrosis factor α (TNF α) regulated pathways comprising an amino acid sequence as shown in FIG. 2b and a TRAF2TD polypeptide which is capable of inhibiting TNF α regulated pathways comprising an amino acid sequence as shown in FIG. 3b.

Another aspect of the present invention provides a method of inhibiting TNF α regulated pathways in a patient comprising introducing into the body of the patient a composition which is capable of inhibiting the TNF α regulated pathway and which comprises an expression vector capable of expressing TRAF2TR polypeptide, an expression vector capable of expressing TRAF2TD polypeptide, a TRAF2TR polypeptide and a pharmaceutically acceptable carrier, or a TRAF2TD polypeptide and a pharmaceutically acceptable carrier.

Still another aspect of the present invention provides a method of inhibiting diseases involving overproduction of TNF α comprising administering to a patient a composition which is capable of inhibiting TNF α regulated pathways and which comprises an expression-vector capable of expressing TRAF2TR, an expression vector capable of expressing TRAF2TD, a TRAF2TR polypeptide and a pharmaceutically acceptable carrier, or a TRAF2TD polypeptide and a pharmaceutically acceptable carrier.

Yet another aspect of the present invention provides a method of inhibiting TNF α pathologies involving hyperactivation of nuclear factor κB(NFκB) dependent genes comprising administering to a patient a composition which is capable of inhibiting TNF α regulated pathways and which comprises an expression vector capable of expressing TRAF2TR, an expression vector capable of expressing. TRAF2TD, a TRAF2TR polypeptide and a pharmaceutically acceptable carrier, or a TRAF2TD polypeptide and a pharmaceutically acceptable carrier.

The present invention also provides a method of inhibiting inflammatory processes involving tumor necrosis factor α comprising administering to a patient a composition which is capable of inhibiting TNF α regulated pathways and which comprises an expression vector capable of expressing TRAF2TR, an expression vector capable of expressing TRAF2TD, a TRAF2TR polypeptide and a pharmaceutically acceptable carrier, or a TRAF2TR polypeptide and a pharmaceutically acceptable carrier.

In certain embodiments, the inflammatory process is selected from the group consisting of Crohn's disease, psoriasis, rheumatoid arthritis, graft versus host disease, inflammatory bowel disease, non-insulin dependent diabetes and neurogenerative diseases.

In yet another embodiment, the inflammatory process is a cardiovascular disease selected from the group consisting of (a) cardiac ischemia-reperfusion injury following myocardial infarction, coronary artery bypass surgery, cardiac transplantation or ischemia-reperfusion injury in the CNS following stroke; (b) the progression and rupture of advanced coronary atherosclerotic plaques; (c) the development and progression of congestive heart failure; (d) endothelial cell injury following balloon angioplasty; and (e) apoptotic cell death of myocardial cells.

In yet another embodiment of the present invention, there is provided a DNA sequence encoding a TRAF2TR/2TD variant.

Another aspect of the present invention provides a TRAF2TR/2TD variant polypeptide which is capable of inhibiting TNF α-regulated pathways.

The present invention provides the advantage of being able to treat a wide variety of disease states using variants of a naturally-occurring protein which interferes with an early event common to these disease states, i.e., TNF α signal transduction.

BRIEF DESCRIPTION OF THE DRAWING

FIGS. 2a and 2b are the nucleic acid sequence (2a) of TRAF2TR cDNA and the amino acid sequence of TRAF2TR (2b).

FIGS. 3a and 3b are the nucleic acid sequence of TRAF2TD (3a) and the amino acid sequence of TRAF2TD (3b).

FIGS. 4a and 4b are the nucleic acid (4a) and amino acid (4b) alignment of spliced TRAF2 (TRAF2TR) and full length TRAF2.

Figure 1:
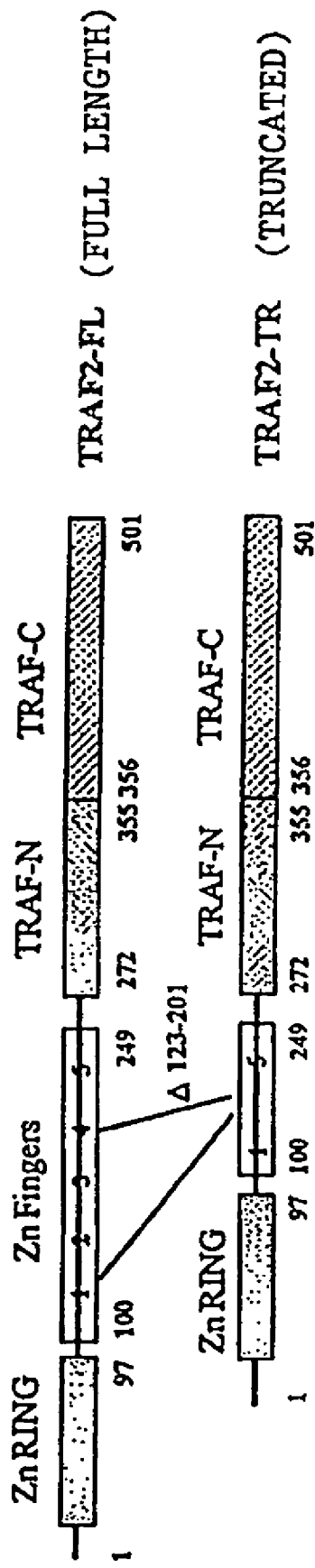
FIG. 1 is a schematic structure of full length TRAF2 (TRAF2-FL) and the alternatively spliced variant, TRAF2TR.

TR overexpression blocks formation of NF-kB and, as a result, no shift has been detected in TNF α stimulated cells (lanes 5 and 6).

DETAILED DESCRIPTION OF THE INVENTION

There are set forth hereafter definitions of terms used herein and descriptions of preferred embodiments of the present invention.

Definitions

A "cloning vector" is a replicon, for example, a plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. A cloning vector may be capable of replication in one cell type and expression in another ("shuttle vector"). In preferred embodiments of the present invention, the cloning vector is capable of expression in a host cell and the "expression vector" is able to express TRAF2TR or TRAF2TD at sufficient levels to interfere with a TNF α regulated pathway in the cell.

A "cassette" refers to a segment of DNA that can be inserted into a vector at one or more specific restriction sites. The segment of DNA encodes a polypeptide of interest and the cassette and restriction sites are designed to ensure insertion of the cassette in the proper reading frame for transcription and translation.

A cell has been "transfected" by exogenous or heterologous DNA when such DNA has been introduced inside the cell. A cell has been. "transformed" by exogenous or heterologous DNA when the transfected DNA effects a phenotypic change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or of deoxyribonucleosides (deoxyadenosine, deoxyguanosine, deoxythymidine, or deoxycytidine; "DNA molecules") or of any phosphoester analogs thereof, such as phosphorothioates and thioesters, in either single stranded form or a double-stranded helix. Double stranded DNA-DNA, DNA-RNA and RNA-RNA helices are possible. The term "nucleic acid molecule" and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, for example, a cDNA, genomic DNA, or RNA, when a single stranded form of the nucleic acid molecule can anneal to the other nucleic acid molecule under the appropriate conditions of temperature and solution ionic strength (see Sambrook et al., infra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art.

As used herein, the term "oligonucleotide" refers to a nucleic acid, generally of at least 18 nucleotides, that is hybridizable to a genomic DNA molecule, a cDNA molecule, or an mRNA molecule encoding TRAF2. Oligonucleotides can be labeled, e.g., with $^{32}P$-nucleotides or nucleotides to which a label, such as biotin, has been covalently conjugated. In one embodiment, a labeled oligonucleotide can be used as a probe to detect the presence of a nucleic acid encoding TRAF2. In another embodiment, oligonucleotides (one or both of which may be labeled) can be used as PCR primers, either for cloning full length or a fragment of TRAF2, or to detect the presence of nucleic acids encoding TRAF2. In a further embodiment, an oligonucleotide can form a triple helix with a TRAF2 DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA "coding sequence" is a double-stranded DNA sequence which is transcribed and translated into a polypeptide in a cell in vitro or in vivo when placed under the control of appropriate regulatory sequences. The DNA coding sequences and the appropriate regulatory sequences are preferably provided in an expression vector. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as, for example, promoters, enhancers, and terminators that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then spliced (if the coding sequence contains introns) and translated into the protein encoded by the coding sequence.

As used herein, the term "homologous" refers to the relationship between proteins that possess a "common evolutionary origin." Such proteins (and their encoding genes) have sequence homology, as reflected by their high degree of sequence similarity. The term "sequence similarity" refers to the degree of identity or correspondence between nucleic acid or amino acid sequences of proteins that may or may not share a common evolutionary origin. However, in common usage and as used herein, the term "homologous," when modified with an adverb such as "highly," may refer to sequence similarity and not a common evolutionary origin.

The term "TNF α regulated pathway" and related terms refer to signal transduction pathways involving the binding of TNF α to a member of the tumor necrosis factor receptor family (TNFR).

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity and not the numbering of the amino acid residues or nucleotide bases.

The term "splice variant" refers to a polypeptide encoded by an mRNA produced by alternative processing of the full length mRNA encoded by a gene or genes resulting in an mRNA that contains one or more deletions relative to the full length mRNA for the genes.

Embodiments of the Invention

The present invention relates to two variants of TRAF2 which inhibit TNF α signaling pathways. One embodiment is an RNA processing splice variant of TRAF2 referred to hereinafter as "TRAF2 truncated" or "TRAF2TR". Another embodiment is based on TRAF2TR having a deletion of amino acid residues 1 to 87 relative to TRAF2TR and is referred to as "TRAF2 truncated-deleted" or "TRAF2TD". Both TRAF2TR and TRAF2TD have the ability to inhibit TNF α signaling pathways. TRAF2TD is a particularly preferred embodiment due to its ability to dramatically reduce the response to TNF α binding.

There follows hereinbelow a description of the structure of these two embodiments, followed by a discussion on how to prepare these embodiments.

Structure and Preparation of TRAF2TR Embodiment

The cDNA sequence for this splice variant is presented in FIG. 2a and the amino acid sequence is presented in FIG. 2b. Referring to FIG. 1 which shows TRAF2TR schematically, it can be seen that the deletion removes amino acid residues 123 to 201 of TRAF2FL, which encompasses the C-terminal portion of Zn finger domain 1 and all of the Zn fingers 2 and 3, as well as the N-terminal residues of Zn finger 4.

The TRAF2TR embodiment of the present invention can be prepared by any suitable method, including a variety of methods known to those of skill in the art. Teachings on the isolation, cloning and sequencing DNA can be found in a variety of sources. General molecular biology, microbiology and recombinant DNA techniques within the skill of the art, are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Given the information in the description herein on the DNA sequence of TRAF2TR and the known methods in the art for obtaining cDNA, nucleotide sequences encoding TRAF2TR and TRAF2TD can be cloned readily or prepared from wild type TRAF2 and inserted into an appropriate vector for expression of these proteins in vitro or in vivo. For a description of methods relating to cloning cDNA and expression vectors, see Sambrook et al., 1989, supra.

A gene encoding TRAF2, whether genomic DNA or cDNA, can be isolated from a human genomic library or cDNA library. Methods for obtaining a gene given the DNA sequence information presented herein are well known in the art. The TRAF2 DNA may be obtained by standard procedures known in the art from cloned DNA (e.g., a DNA "library"). It is obtained preferably from a cDNA library prepared from tissues with high level expression of the protein (e.g., cells of lymphoid origin, in particular, B cells or an osteosarcoma cell line, for example, human osteosarcoma SAOS-2 (ATCC No. HTB-85) that exhibit high levels of expression of TRAF2 or TRAF2TR). The DNA may also be obtained by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II) or by chemical synthesis. Clones derived from genomic DNA may contain regulatory and intron DNA regions in addition to coding regions; clones derived from cDNA will not contain intron sequences. Given that the present invention is based in part on the isolation of a splice variant. (TRAF2TR) of full length TRAF2, it is desirable to obtain a cDNA encoding the TRAF2TR sequence.

Methods for obtaining cDNA are well known in the art. Briefly, these methods include isolating a mixture of messenger RNA (mRNAs) from eukaryotic cells and employing a series of enzymatic reactions to synthesize double-stranded DNA copies (cDNAs) complementary to the isolated mRNAs.

It has been found that reverse transcriptase-polymerase chain reaction (RT-PCR) cloning is an efficient way to isolate cDNA containing the TRAF2TR splice variant as presented in Example 1 hereinbelow. RT-PCR involves reverse transcription of cellular mRNA with the enzyme reverse transcriptase followed by subjecting the resultant DNA product to amplification using PCR.

Regardless of the method used to obtain the desired cDNA, the double-stranded cDNA mixture is inserted into cloning vehicles by any one of many known techniques, depending at least in part on the particular vehicle used. Various insertion methods are discussed in considerable detail in *Methods in Enzymology*, 68, 16-18 (1980), as well as in Sambrook et al., 1989, supra.

Once the DNA segments are inserted into a cloning vehicle, the cloning vehicle is used to transform a suitable host. These cloning vehicles usually impart an antibiotic resistance trait on the host. Such hosts are generally prokaryotic cells and only a few of the host cells contain the desired cDNA. The transfected host cells constitute a gene "library", providing a representative sample of the mRNAs present in the cell from which the mRNAs were isolated.

Given the sequence information on TRAF2 provided herein, an appropriate oligonucleotide sequence may be prepared, preferably synthesized as discussed above, and used to identify clones containing TRAF2 sequences. To identify clones containing the TRAF2 sequences, individual transformed or transfected cells are grown as colonies on a nitrocellulose filter paper. The colonies are lysed and the DNA is bound tightly to the filter paper by heating. The filter paper is then incubated with a labeled oligonucleotide probe which is complementary to TRAF2. DNA fragments with substantial homology to TRAF2 will hybridize to the probe. The greater the degree of homology, the more stringent hybridization conditions can be used.

The probe hybridizes with the cDNA for which it is complementary. It can be identified by autoradiography or by chemical reactions that identify the presence of the probe. The corresponding clones are characterized in order to identify one or a combination of clones which contain all of the structural information for the desired protein. The nucleic acid sequence coding for the protein of interest is isolated and reinserted into an expression vector. The expression vector brings the cloned gene under the regulatory control of specific prokaryotic or eukaryotic control elements which allow the efficient expression (transcription and translation) of the ds-cDNA.

Further selection can be carried out on the basis of the properties of the gene. For example, if the gene encodes a protein product having the isoelectric, electrophoretic, amino acid composition, or partial amino acid sequence of the TRAF2 protein as disclosed herein. Thus, the presence of the gene may be detected by assays based on the physical, chemical, or immunological properties of its expressed product. For example, cDNA clones, or DNA clones can be selected which produce a protein that has similar or identical properties to TRAF2TR with regard to electrophoretic migration, isoelectric focusing, non-equilibrium pH gel electrophoresis, proteolytic digestion, or antigenicity.

Structure and Preparation of TRAF2TD Embodiment

Relative to TRAF2TR, TRAF2TD has a deletion of amino acids 1 to 87 and the corresponding nucleotides encoding these amino acids. The DNA sequence for TRAF2TD is presented in FIG. 3a and the amino acid sequence is presented in FIG. 3b.

Any suitable method can be used to prepare the TRAF2TD embodiment, including, for example, a variety of methods based on the information provided above. In particular, there are a number of methods for creating a truncated version of TRAF2TR containing a deletion of amino acids 1 to 87. In a preferred method of preparation, TRAF2TR cDNA is used as a template for PCR using a 5' primer encompassing nucleotides 262 to 280 of the TRAF2 full length coding sequence (ATGAGTTCGGCCTTCCCA-GAT wherein the ATG codon was included to create a translation initiation site; the 3' primer was TTA TAG CCC TGT CAG GTC CAC. The resulting construct begins at amino acid 88 of full length TRAF2 and contains the 123 to 201 amino acid deletion of TRAF2TR.

Additional variants of TRAF2TR can be prepared using methods such as those described above for the preparation of TRAF2TD.

TRAF2TR/2TD Variants

The present invention includes within its scope allelic variants, substitution, addition and deletion mutant variants, analogs, and derivatives of TRAF2TR or TRAF2TD (hereinafter referred to as "TRAF2TR/2TD variants") and homologs from other species that have the same or homologous functional activity as TRAF2TR. In preferred embodiments, genes having deletions or substitutions that increase the ability to inhibit TNF α signaling pathways are utilized in the practice of the invention. Preparation or isolation of TRAF2TR/2TD variants are within the scope of the present invention. Accordingly, the scope of the present invention includes TRAF2TR/2TD variants which are functionally active, i.e., capable of exhibiting one or more functional activities associated with TRAF2TR.

TRAF2TR/2TD variants can be made by altering encoding nucleic acid sequences by substitutions, additions or deletions that provide for functionally equivalent molecules. Preferably, TRAF2TR/2TD embodiments are made that have enhanced or increased functional activity relative to TRAF2TR or TRAF2TD.

Due to the degeneracy of nucleotide coding sequences, other DNA sequences which encode substantially the same amino acid sequence as TRAF2TR, including an amino acid sequence that contains a single amino acid variant, may be used in the practice of the present invention. These include, but are not limited to, allelic genes, homologous genes from other species, and nucleotide sequences comprising all or portions of TRAF2TR which are altered by the substitution of different codons that encode the same amino acid residue within the sequence, thus producing a silent change. Likewise, the TRAF2TR/2TD variants of the invention include, but are not limited to, those containing, as a primary amino acid sequence, all or part of the amino acid sequence of a TRAF2TR protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding TRAF2TR/2TD variants of the invention can be produced by various methods known in the art. The manipulations which result in their production can occur at the gene or protein level. For example, the cloned TRAF2 gene sequence can be modified by any of numerous strategies known in the art (Sambrook et al., 1989, supra).

The sequence can be cleaved at appropriate sites with restriction endonuclease(s), followed by further enzymatic modification if desired, isolated, and ligated in vitro. In the production of the gene encoding a TRAF2TR/2TD embodiment, care should be taken to ensure that the modified gene remains within the same translational reading frame as the TRAF2TR gene, uninterrupted by translational stop signals, in the gene region where the desired activity is encoded.

Additionally, the TRAF2TR/2TD-encoding nucleic acid sequence can be mutated in vitro or in vivo to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated TRAF2TR gene product. Any technique for mutagenesis known in the art can be used, including but not limited to, in vitro site-directed mutagenesis (Hutchinson, C., et al., 1978, *J. Biol. Chem.* 253:6551; Zoller and Smith, 1984, *DNA* 3:479-488; Oliphant et al., 1986, *Gene* 44:177; Hutchinson et al., 1986, *Proc. Natl. Acad. Sci. U.S.A.* 83:710), use of "TAB" linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The discussion which follows relates to the manipulation and expression of DNA encoding the desired polypeptides is common to both TRAF2TR and TRAF2TD, as well as TRAF2TR/2TD variants.

Cloning of TRAF2TR, TRAF2TD and TRAF2TR/2TD Variants into Cloning/Expression Vectors The identified and isolated DNA sequence can be inserted into an appropriate cloning/expression vector (hereinafter "vector") to facilitate modifications to the sequence or expression of the protein. These vectors typically include multiple cloning sites, promoters, sequences which facilitate replication in a host cell and selection markers.

Any suitable vector can be used. There are many known in the art. Examples of vectors that can be used include, but are not limited to, plasmids or modified viruses. The vector is typically compatible with a given host cell into which the vector is introduced to facilitate replication of the vector and expression of the encoded proteins. The insertion of a DNA sequence into a given vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Useful vectors may consist of segments of chromosomal, non-chromosomal and synthetic DNA sequences. Examples of specific vectors useful in the practice of the present invention include, but are not limited to, *E. coli bacteriophages*, for example, lambda derivatives, or plasmids, for example, pBR322 derivatives or pUC plasmid derivatives, e.g., pmal-c, pFLAG, derivatives of SV40 and known bacterial plasmids, e.g., *E. coli* plasmids col E1, pCR1, pMal-C2, pET, pGEX (Smith et al., 1988, *Gene* 67:31-40), pMB9 and their derivatives, plasmids such as RP4; phage DNAs, e.g., the numerous derivatives of phage 1, e.g., NM989, and other phage DNA, e.g., M13 and filamentous single stranded phage DNA; yeast vectors such as the 2 µm plasmid or derivatives thereof; vectors useful in eukaryotic cells, for example, vectors useful in insect cells, such as baculovirus vectors, vectors useful in mammalian cells; vectors derived from combinations of plasmids and phage DNAs, plasmids that have been modified to employ phage DNA or other expression control sequences; and the like.

Yeast vectors that can be used according to the invention include, but are not limited to, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen).

Baculovirus vectors that can be used in the practice of the invention include a variety of vectors, including both non-fusion transfer vectors, for example, pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, for example, pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen) can be used.

Mammalian vectors contemplated for use in the invention include, for example, vectors with inducible promoters, for example, the dihydrofolate reductase (DHFR) promoter, e.g., any expression vector with a DHFR expression vector, or a DHFR/methotrexate co-amplification vector, for example, pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, for example, pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, for example, pREP4 (BamH1, SfiI, XhoI, NotI, NheI, HindIII, NheI, PvuII, and KpnI cloning site, constitutive Rous Sarcoma Virus Long Terminal Repeat (RSV-LTR) promoter, hygromycin selectable marker; Invitrogen), pCEP4 (BamH1, SfiI, XhoI, NotI, NheI, HindIII, NheI, PvuII, and KpnI cloning site, constitutive human cytomegalovirus (hCMV) immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), pcDNA3 (HindIII, KpnI, BamHI, BstXI, EcoRI, EcoRV, BstXI [repeat], NotI, XhoI, XbaI, ApaI, cloning sites, G418, ampicillin selection, Invitrogen) and others. Vaccinia virus mammalian expression vectors (see, Kaufman, 1991, supra) for use according to the invention include but are not limited to pSC11 (SmaI cloning site; TK- and β-gal selection), pMJ601 (SalI, SmaI, AflI, NarI, BspMII, BamHII, ApaI, NhrI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

A variety of methods may be used to confirm that the desired DNA sequence encoding TRAF2TR, TRAF2TD or TRAF2TR/2TD variants have been cloned into a vector. In general, one or more of the following approaches is used: (a) PCR amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding TRAF2TR is inserted within the "selection marker" gene sequence of the vector, recombinants containing the TRAF2TR insert can be identified by the absence of the selection marker gene function. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

Promoters

The nucleotide sequence coding for TRAF2TR or TRAF2TD or a TRAF2TR/2TD variant thereof can be inserted into an expression vector which contains the necessary elements for the transcription and translation of the inserted protein-coding sequence. Such elements are termed herein a "promoter." Thus, the nucleic acid encoding the polypeptides of the invention is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector, or they may be supplied by the native gene encoding TRAF2 and/or its flanking regions. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression may be controlled by any promoter/enhancer element known in the art, but these regulatory elements must be functional in the host selected for expression. Promoters which may be used to control TRAF2TR gene expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors for example, the β-lactamase promoter (Villa-Kamaroff, et al., 1978, Proc. Natl. Acad. Sci. U.S.A., 75:3727-3731), or the tac promoter (DeBoer, et al., 1983, Proc. Natl. Acad. Sci. U.S.A., 80:21-25); see also "Useful proteins from recombinant bacteria" in Scientific American, 1980, 242:74-94; promoter elements from yeast or other fungi for example, the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol., 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol., 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol., 5:1639-1648; Hammer et al., 1987, Science 235:53-58), alpha 1-antitrypsin gene control region which is active in the liver (Kelsey et al., 1987, Genes and Devel., 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Introduction of Vectors into Host Cells

Vectors can be introduced into host cells by any suitable method, including, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990), so that many copies of the gene sequence are generated. Preferably, the cloned gene is contained on a shuttle vector plasmid, which provides for expansion in a cloning cell, e.g., E. coli, and facilitates purification for subsequent insertion into an appropriate expression cell line. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 µm plasmid.

Host Cell Systems

Potential host cell systems include but are not limited to mammalian host cell systems infected with virus (e.g., vaccinia virus, adenovirus, etc.); insect host cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host cell system utilized, any one of a number of suitable transcription and translation elements may be used.

In addition, a host cell strain may be chosen which modulates the expression of the inserted sequences, or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. Expression in yeast can produce a biologically active product. Expression in eukaryotic cells can increase the likelihood of "native" folding. Moreover, expression in mammalian cells can provide a tool for reconstituting, or constituting, TRAF2TR-inhibiting activity. Furthermore, different vector/host expression systems may affect processing reactions, such as proteolytic cleavages, to a different extent. Expression vectors of the invention can be used, as pointed out above, both to transfect cells for screening or biological testing of modulators of TRAF2TR activity.

A recombinant TRAF2TR, TRAF2TD or TRAF2TR/2TD variant of the invention may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding TRAF2TR is introduced is cultured in an appropriate cell culture medium under conditions that provide for expression of TRAF2TR by the cell.

Once a suitable host system and growth conditions are established, recombinant expression vectors can be propagated and prepared in quantity. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, including polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

As discussed above, a "vector" is any means for the transfer of a nucleic acid according to the invention into a host cell. Preferred vectors are viral vectors, for example, retroviruses, herpes viruses, adenoviruses, and adeno-associated viruses. Thus, a gene encoding a protein or polypeptide domain fragment of the present invention is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Use of Viral Vector Systems for

Ex Vivo and In Vivo Treatment Methods

Viral vectors commonly used for in vivo or ex vivo targeting and therapy procedures are DNA-based vectors and retroviral vectors. Methods for constructing and using viral vectors are known in the art [see, e.g., Miller and Rosman, *BioTechniques* 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Defective viruses, which entirely or almost entirely lack viral genes, are preferred. Defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1), vector [Kaplitt et al., *Molec. Cell. Neurosci.* 2:320-330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626-630 (1992); see also La Salle et al., *Science* 259:988-990 (1993)]; and a defective adeno-associated virus vector [Samulski et al., *J. Virol.* 61:3096-3101 (1987); Samulski et al., *J. Virol.* 63:3822-3828 (1989); Lebkowski et al., *Mol. Cell. Biol.* 8:3988-3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-g (IFN-g), or anti-CD4 antibody, can be administered to block humoral or cellular immune responses to the viral vectors [see, e.g., Wilson, Nature Medicine (1995)]. In addition, it is advantageous to employ a viral vector that is engineered to express a minimal number of antigens.

Naturally, the invention contemplates delivery of a vector that will express a therapeutically effective amount of TRAF2TR for gene therapy applications. The phrase "therapeutically effective amount" is used herein to mean an amount sufficient to reduce and most preferably prevent an immune response resulting in a clinically significant manifestation of a disease linked to TNF α binding. Alternatively, a therapeutically effective amount is sufficient to cause an improvement in a clinically significant condition in the host.

Preferred Viral Vector Systems
Used in Ex Vivo and In Vivo Treatment Methods

Certain viral vector systems are well developed in the art and are suited to the treatment methods of the present invention.

a. Adenovirus Vector Systems

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., *Virology* 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfI-Sau3A fragment). Other regions may also be modified, in particular the E3 region (WO95/02697), the E2 region (WO94/28938), the E4 region (WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic-acid sequence are inserted (see FR94 13355, the contents of which are incorporated herein by reference).

The replication defective recombinant adenoviruses according to the invention can be prepared by any technique known to the person skilled in the art (Levrero et al., *Gene* 101 (1991) 195, EP 185 573; Graham, *EMBO J*. 3 (1984) 2917). In particular, they can be prepared by homologous recombination between an adenovirus and a plasmid which carries, inter alia, the DNA sequence of interest. The homologous recombination is effected following cotransfection of the adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., *J. Gen. Virol.* 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

b. Adeno-Associated Virus Vector Systems

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterised. It encompasses approximately 4700 bases and contains an inverted terminal repeat (ITR) region of approximately 145 bases at each end, which serves as an origin of replication for the virus. The remainder of the genome is divided into two essential regions which carry the encapsulation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsulation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a nucleic acid encoding TRAF2TR or TRAF2TD flanked by the AAV ITRs. The invention also relates to a plasmid encompassing a sequence encoding a nucleic acid encoding TRAF2TR or TRAF2TD flanked by two ITRs from an AAV. Such a plasmid can be used as it is for transferring the nucleic acid sequence, with the plasmid, where appropriate, being incorporated into a liposomal vector (pseudo-virus).

c. Retrovirus Vector Systems

In another embodiment the gene can be introduced in a retroviral vector, e.g., as described in Anderson et al., U.S. Pat. No. 5,399,346; Mann et al., 1983, *Cell* 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; EP 453242, EP178220;

Bernstein et al. *Genet. Eng.* 7 (1985) 235; McCormick, *BioTechnology* 3 (1985) 689; International Patent Publication No. WO 95/07358, published Mar. 16, 1995, by Dougherty et al.; and Kuo et al., 1993, *Blood* 82:845. The retroviruses are integrating viruses which infect dividing cells. The retrovirus genome includes two LTRs an encapsulation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsulation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsulation sequences which may include a part of the gag gene (Bender et al., *J. Virol.* 61 (1987) 1639). Recombinant retroviral vectors are purified by standard techniques known to those having ordinary skill in the art.

Retroviral vectors can be constructed to function as infections particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus. Targeted gene delivery is described in International Patent Publication WO 95/28494, published October 1995.

Non-Viral Systems Used in

Ex Vivo and In Vivo Treatment Methods

Certain non-viral systems have been used in the art and can facilitate introduction of DNA encoding the polypeptides of the present invention to desired target cells.

a. Lipofection Delivery Systems

A vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413-7417 (1987); see Mackey, et al., *Proc. Natl. Acad. Sci. U.S.A.* 85:8027-8031 (1988); Ulmer et al., *Science* 259:1745-1748 (1993)]. The use of cationic lipids may promote encapsulation of negatively charged nucleic acids, and also promote fusion with negatively charged cell membranes [Felgner and Ringold, *Science* 337:387-388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, for example, pancreas, liver, kidney, and the brain. Lipids may be chemically coupled to other molecules for the purpose of targeting [see Mackey, et. al., supra]. Targeted peptides, e.g., hormones or neurotransmitters, and proteins for example, antibodies, or non-peptide molecules could be coupled to liposomes chemically.

Other molecules are also useful for facilitating transfection of a nucleic acid in vivo, for example, a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

b. Naked DNA Delivery Systems

It is also possible to introduce the vector in vivo as a naked DNA plasmid (see U.S. Pat. Nos. 5,693,622, 5,589,466 and 5,580,859). Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963-967 (1992); Wu and Wu, *J. Biol. Chem.* 263:14621-14624 (1988); Hartmut et al., Canadian Patent Application No. 2,012,311, filed Mar. 15, 1990; Williams et al., *Proc. Natl. Acad. Sci. USA* 88:2726-2730 (1991)]. Receptor-mediated DNA delivery approaches can also be used [Curiel et al., *Hum. Gene Ther.* 3:147-154 (1992); Wu and Wu, *J. Biol. Chem.* 262:4429-4432 (1987)].

Methods to Identify

Therapeutically Useful Variants of TRAF2TR

Figure 7:
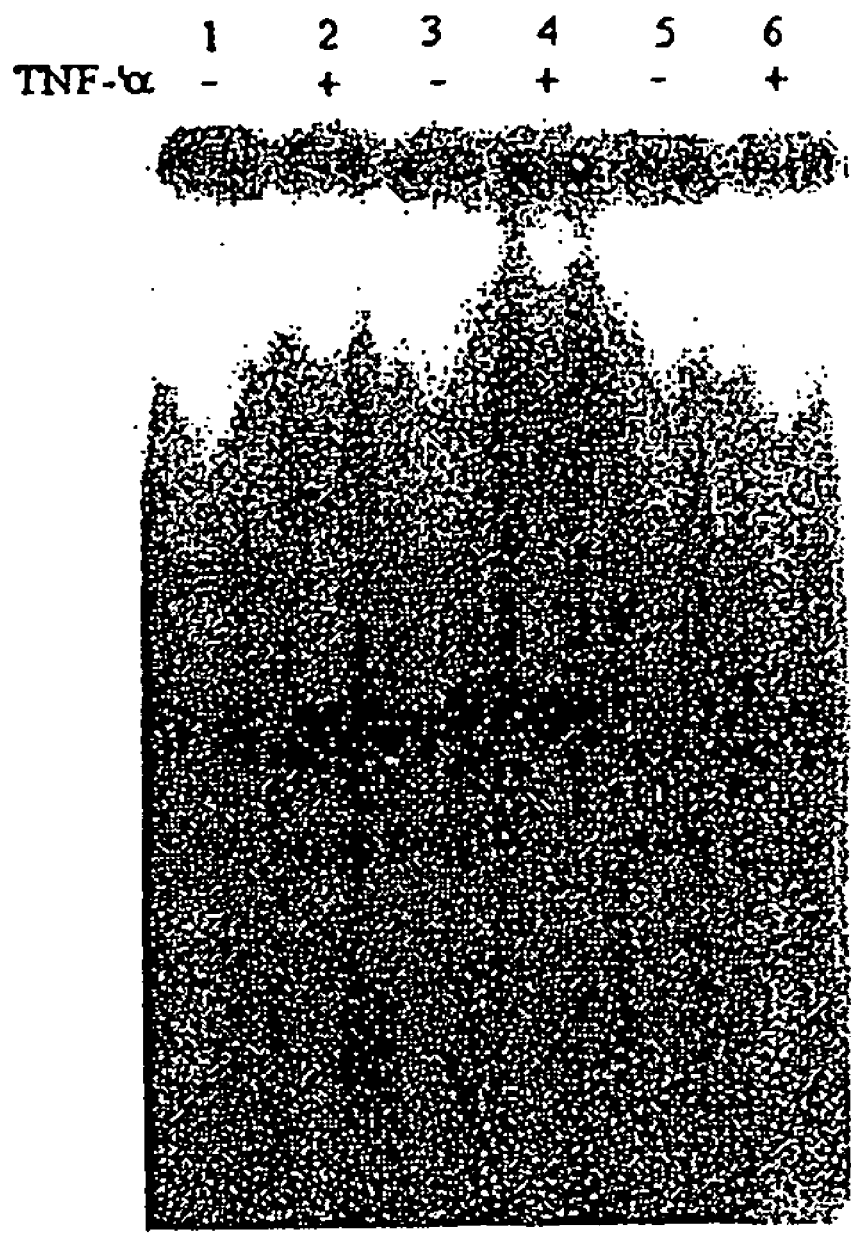
FIG. 7 illustrates an electrophoretic mobility shift assays (EMSA) that was performed using an NFKB UAS probe. Nuclear extracts from cells overexpressing FL TRAF2 (lanes 3 and 4) show TNF-alpha induced shifts significantly stronger in comparison to control (lanes 1 and 2). TRAF2-

There are a variety of methods which may be used to determine whether a TNF α regulated pathway is involved in a disease state and to determine the effect of the polypeptides of the present invention on these pathways. For example, to study the role of TRAF2TR in NFκB regulation, electrophoretic mobility shift assay (EMSA) analysis was performed using NFκB UAS as a probe (FIG. 7). Nuclear extracts from cells overexpressing FL TRAF (lanes 3 and 4) show TNF α induced shifts significantly stronger in comparison to control (lanes 1 and 2). TRAF2TR overexpression blocks formation of NFκB and, as a result, no shift has been detected in TNF α stimulated cells (lanes 5 and 6). These results suggested strong inhibition of NFκB formation as no shift band appeared in TNF α stimulated-cells. Increase amount of NF KB binding activity is present in cells overexpressing full-length TRAF2 after stimulation with TNF α (lane 4).

Experiments of the type discussed hereinabove can be utilized to determine whether a given pathway implicated in a disease state might be treated using the compositions of the present invention. In general, the experiments described above can be performed substituting TRAF2TR or TRAF2TD with an isolated or prepared variant of TRAF2 to determine if the variant has the ability to inhibit TNF α regulated pathways.

Disease States Related to TNF α Regulated Pathways

As discussed above, the present invention relates to the use of TRAF2TR and TRAF2TD and variants thereof to inhibit TNF α regulated pathways. In particular, the present invention relates to using the aforementioned to effectively block TNF α induced activation of several transcriptional factors, including NFκB and AP-1. TRAF2TR and TRAF2TD and variants thereof are useful in inhibiting TNF α signal transduction pathways in pathologies which involve overproduction of TNF α and hyperactivation of NFκB dependent genes. A variety of diseases appear to involve TNF α regulated pathways and the pathological basis for these diseases may involve overproduction of TNF α or hyperactivation of NFκB dependent genes. These diseases can be treated using the TRAF2TR and TRAF2TD proteins and their variants.

Given the evidence that inflammatory processes contribute heavily to the pathology of all the major cardiovascular disease states and given that elevated TNF α levels are associated with these inflammatory processes, it is believed that a variety of major cardiovascular disease states can be treated using the compositions and methods of the present invention. These diseases include, but are not limited to, cardiovascular disease states, including cardiac ischemia-reperfusion injury following myocardial infarction, coronary artery bypass surgery, cardiac transplantation or ischemia-reperfusion injury in the CNS following stroke; the progression and rupture of advanced coronary atherosclerotic plaques; the development and progression of congestive heart failure; and endothelial cell injury following balloon angioplasty. In addition, the present invention can be used to prevent apoptotic cell death of myocardial cells during heart failure or infarction and to avoid myocyte apoptosis.

By blocking TNF α receptor signaling, a gene therapy approach using TRAF2TR or TRAF2TD or a variant thereof can be used to treat these diseases. The use of TRAF2TD is preferred, given its highly effective inhibition of TNF α regulated pathways.

Similarly, by blocking TNF α receptor signaling, gene therapy with TRAF2TR of TRAF2TD or a variant thereof can be used to treat other disease states where TNF α is involved in the pathogenesis. These disease states include, but are not limited to, Crohn's disease, psoriasis, rheumatoid arthritis, graft versus host disease, inflammatory bowel disease, non-insulin dependent diabetes and neurodegenerative diseases (e.g., Parkinson's disease).

Additionally, TRAF2TD can be used in various assays to study the mechanisms of TRAF2-dependent signal transduction pathways.

Therapeutic Compositions and Dosages

In use, any vector, viral or non-viral, of the invention is preferably introduced in vivo in a pharmaceutically acceptable vehicle or carrier. The phrase "pharmaceutically acceptable" refers to molecular entities and compositions that are physiologically tolerable and do not typically produce a significant allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, for example, water and oils, including those of petroleum, animal, vegetable or synthetic origin, for example, peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W; Martin.

The present invention provides methods of treatment which comprise the administration to a human or other animal of an effective amount of a composition of the invention.

Effective amounts may vary, depending on the age, type and severity of the condition to be treated, body weight, desired duration of treatment, method of administration, and other parameters. Effective amounts are determined by a physician or other qualified medical professional.

It is believed that polypeptides according to the invention will be used most widely in doses of about 0.01 mg/kg to about 100 mg/kg of body weight per day. Preferred doses are about 0.1 mg/kg to about 50 mg/kg, with doses of about 1 mg/kg to about 10 mg/kg of body weight per day being more preferred.

Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term "pfu" ("plaque-forming unit") corresponds to the infective power of a suspension of virions and is determined by infecting an appropriate cell culture and measuring the number of plaques formed. The techniques for determining the pfu titre of a viral solution are well documented in the prior art.

The following examples are illustrative of the present invention.

EXAMPLES

Example 1

Isolation of cDNA Encoding TRAF2TR

The TRAF2 splice variant, TRAF2TR, was isolated during RT PCR cloning (*Current Protocols in Molecular Biology*, 1996) of full length TRAF2 using mRNA from the human Osteosarcoma cell line (OSA1). While using primers to produce full length TRAF2 cDNA, a smaller PCR product was observed. The fragment was excised and cloned independently. The 5' primer used for the RT PCR was ATG GCT GCA GCT AGC GTG ACC and the 3' primer was TTA TAG CCC TGT CAG GTC CAC.

Figure 4B:
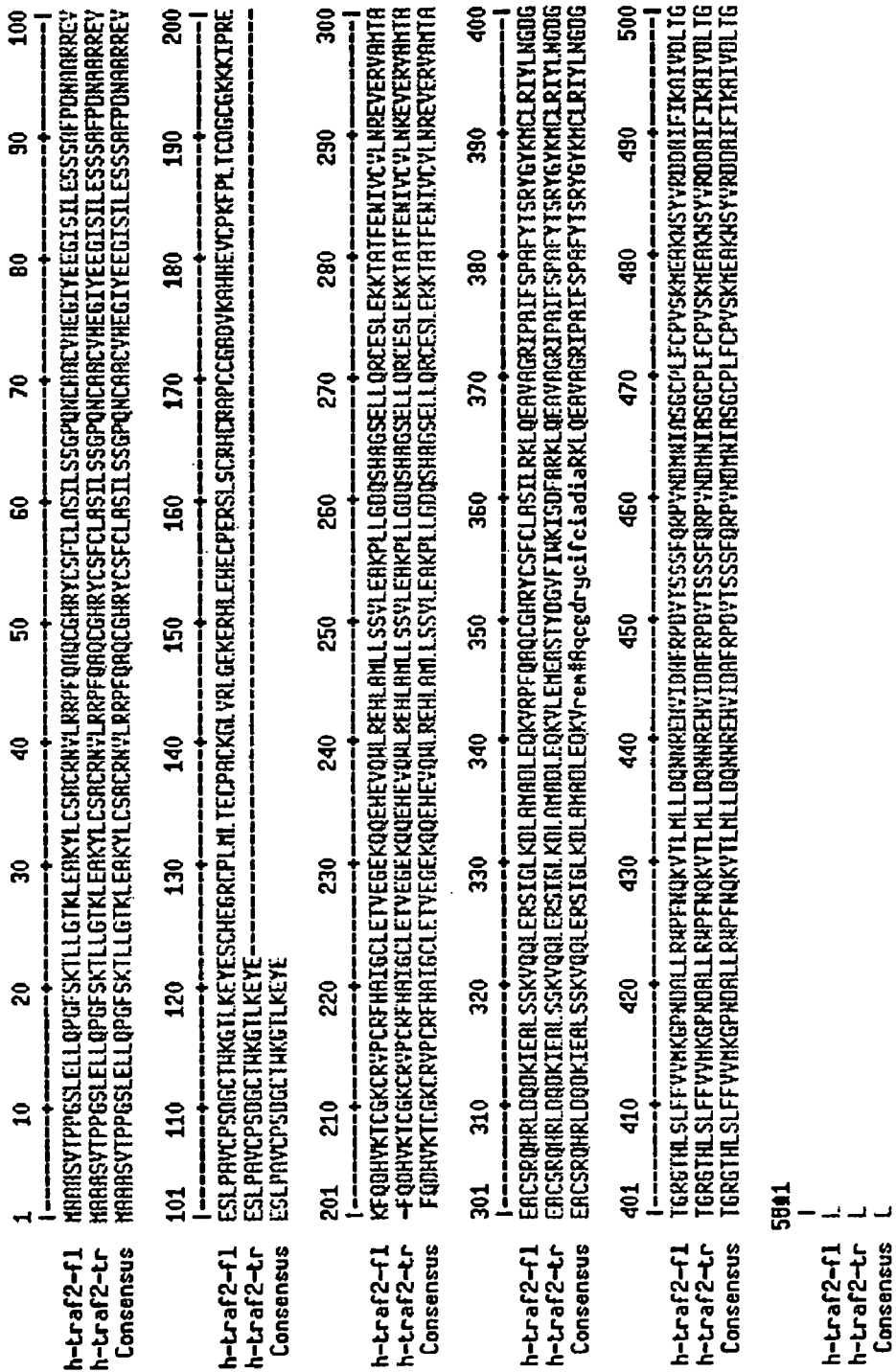

Upon sequencing of this smaller clone (TRAF2TR), an in-frame deletion of the codons encoding amino acid residues 123 to 201 were identified. FIGS. 4*a* and 4*b* compare the nucleic and amino acid sequences of full length TRAF2 and TRAF2TR.

Figure 5:
FIG. 5 illustrates the tissue distribution of TRAF2TR variant mRNA. Lanes: 1—control TRAF2FL cDNA; 2—control TRAF2 spliced variant (TRAF2TR) cDNA; 3-Jurkat; 4-HeLa cell line; 5-Thymus; 6-placenta; 7-Thymus; 8-spleen; 9-ovary; 10-control TRAF2FL.

A variety of tissues in the body have been identified as sources of TRAF2TR mRNA and may be used to isolate the TRAF2TR mRNA using the protocol described above. To determine the tissue distribution of TRAF2TR, RT-PCR was performed using a pair of primers outside of the spliced region. The primer on the 5' side of the deletion was: GGT GGA GAG CCT GCC GGC CG and the primer on the 3' side of the deletion was: GGC AGC CGA TGG CGT GGA ATC TG, and cDNA was generated using an oligo-dT primer from total RNA from different tissues. The cDNAs were separated by agar electrophoresis and transferred to nitrocellulose. Hybridization was performed using a specific probe from the TRAF2 sequence adjacent to the 5' end of the spliced region (5'-GAT GCA CCT GGA AGG GGA CCC TGA AAT-3'). This probe recognizes both non-spliced and spliced variants of TRAF2. The expected size for the non-spliced variant (TRAF2FL) is 373 bp and for the spliced variant (TRAF2TR), 136 bp. Referring now to FIG. 5, Lanes: 1-control TRAF2-FL cDNA; 2-control TRAF2 spliced variant cDNA; 3-Jurkat; 4-HeLa cell line; 5-thymus; 6-placenta; 7-thymus; 8-spleen; 9-ovary.

Western blot analysis of lysates from various cell sources does not unequivocally detect the presence of the truncated TRAF2 variant at the level of expressed protein. It appears that the high level expression and production of the protein are limited developmentally, temporally, or controlled by an undefined mechanism, in a cell type dependent manner (e.g., B cell maturation in Germinal centers).

The deletion in the splice variant TRAF2TR retains an open reading frame and the 5' splice boundary matches canonical splice donor sequence. The deletion removes amino acid residues 123-201 of WT TRAF2, which encompasses the C-terminal portion of zinc finger domain 1 and all of zinc fingers 2 and 3 as well as the N-terminal residues of zinc finger 4 (FIG. 1). This deletion more than likely disrupts the function of the zinc finger region, and is similar to the deletion created by Takeuchi et al., *J. Biol. Chem.* 271(33), 19935-19942 (1996) which they report exhibits a dominant negative effect on TNF α induced NFKB activation.

Example 2

Preparation of TRAF2TD

It is known that deletion of N-amino terminal 87 amino acids (representing the ring fingers domain, see FIG. 1) of TRAF2 creates a protein which acts as a dominant inhibitor (dominant negative) of TNF α dependent NFκB activation (Takeuchi et al., *J. Biol. Chem.* 271(33), 19935-19942 (1996)). In order to determine if an N-terminal deletion would affect the activity of TRAF2TR, a construct representing TRAF2TR with a deletion of 87 amino acids from the N-terminus of the protein (residues 1 to 87) was prepared. To prepare this variant of TRAF2TR, TRAF2TR cDNA was used as a template for PCR using a 5' primer encompassing nucleotides 262 to 280 of the TRAF2 full length coding sequence (ATGAGTTCGGCCTTCCCAGAT wherein the ATG codon was included to create a translation initiation site; the 3' primer was TTA TAG CCC TGT CAG GTC CAC. The resulting construct begins at amino acid 88 of full length TRAF2 and contains the 123 to 201 amino acid deletion of TRAF2TR, providing a "double deletion" construct. The construct was verified by DNA sequencing and cloned into a mammalian expression vector (pcDNA3, Invitrogen).

Example 3

Transfection of HeLa Cells with TRAF2TR

To determine the effect of TRAF2TR on NFκB activation, truncated as well as the full length (FL) TRAF2 were constructed with N-Myc affinity tags in a mammalian expression vector (pcDNA3, INVITROGEN). To prepare N-myc fusion constructs, a 5' PCR primer was synthesized containing the sequence of the Myc tag with a starting methionine (MetGluGlnLysLeuIleSerGluGluAspLeuAsn) followed by the first nucleotides of the TRAF2 cDNA: 5'-ATG GAG CAG AAA TTG ATT TCC GAG GAA GAT CTG AAC ATG GCT GCA GCT AGC GTG AC-3'. The 3' PCR primer sequence was: 5'-TTAGAGCCCTGTCAG-GTCCACAA-3'. The PCR product was purified and cloned into the pcDNA3 vector using standard techniques.

HeLa cells were transfected with pcDNA3-myc TRAF2 constructs using LipoFectamine (BRL, Gibco) reagent using the protocol provided by the reagent supplier. In brief, 4 ml of LipoFectamine were mixed with 1 mg of the DNA in 1 ml of Serum free DMEM (BRL) media and $3 \times 10^5$ cells in 60 mm Petri dish were incubated with that mixture overnight at 37° C. at 5% $CO_2$ incubator. Twenty-four hours after transfection, cells were washed with phosphate buffered saline and lysed in 200 ml of an SDS electrophoresis sample buffer (SIGMA). Ten ml of the lysate was separated by electrophoresis and Western blotted to a nitrocellulose membrane. Immunostaining and ECL (AMERSHAM) detection was performed according to the recommendations of the antibody supplier.

Figure 6:
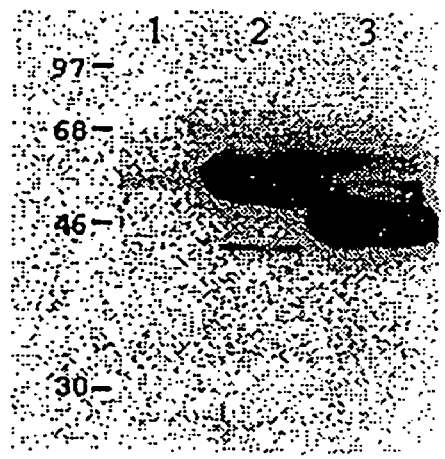
FIG. 6 illustrates the immunodetection of Myc-fused TRAF2FL and TRAF2TR in transfected HeLa cells. Lanes: 1-pcDNA3 vector; 2-myc-TRAF2FL; 3-myc-TRAF2TR.

Anti-Myc antibodies (BABCO, Berkeley) detected proteins of the expected size in HeLa cells transfected with pcDNA-TRAF2FL and pcDNA-TRAF2TR (FIG. 6).

The results, shown in FIG. 6, show the immunodetection of Myc-fused TRAF2FL and TRAF2TR in transfected HeLa cells. HeLa cells were transfected with expression constructs of TRAF-FL and TRAF-TR using lipofectamine (Gibco BFL) and after 24 hours cells were lysed in SDS loading buffer. Myc-fusion proteins were detected using anti-myc Ab and ECL detection system. Lanes: 1-pcDNA3 vector; 2-myc-TRAF2FL; 3-myc-TRAF2TR.

Example 4

NFκB Reporter System

In order to determine the effect of TRAF2TR, TRAF2TD or variants of these polypeptides on NFκB regulated gene expression, an NFκB reporter system can be used, such as the system utilized and described in Takeuchi et al., *J. Biol. Chem.*, 271(33), 19935-42 (1996). An NFκB reporter activation system may be utilized in conjunction with appropriate cells, such as 293 cells, COS7 cells or HeLa cells. The cells would be transfected with different TRAF2 constructs, i.e., full length TRAF2, TRAF2TR and TRAF2TD, using the lipofectamine protocol discussed in Example 3. The effect of the different TRAF2 fragments on activation of a cotransfected NFκB reporter can then be compared to identify the most effective inhibitor species. As an example, TRAF2 constructs comprising full length TRAF2, TRAF2TR and TRAF2TD, as well as variants of TRAF2TR and TRAF2TD, can be transfected into 293 cells and the level of NFκB reporter activity monitored in the presence or absence of TNFα. The full-length TRAF2 would be expected to activate the cotransfected NFκB reporter while the other TRAF2 constructs would be expected to block TNF α mediated activation of the NFκB reporter to varying degrees.

Example 5

Ex Vivo Treatment Methods

Methods of ex vivo gene therapy are known in the art and generally involve four stages. In the first stage, cells of a given type are collected from the patient to be treated. In the second stage, the desired gene is transfected into the isolated cells. In the third stage, those cells which have taken up the desired gene are selected and grown. In the fourth stage, the cells are either infused or transplanted back into the patient where they express the desired gene and treat the disease.

In the first stage of an ex vivo treatment method utilizing the present invention, cells are obtained from the patient. The choice of cell is based on a number of factors, primarily the specific disease being treated. Blocking activation in these target cells would inhibit expression of pro-inflammatory cytokines and other proteins involved in the inflammatory processes linked to manifestation of a cardiovascular disease state.

In the second stage, the TRAF2TR or TRAF2TD or variant cDNA is cloned into an appropriate mammalian expression vector. For transfection protocols involving lipofection, an expression vector, for example, pcDNA3 can be used. In a preferred embodiment, TRAF2TD, given its enhanced ability to inhibit TNF α binding effects, is cloned into pcDNA3 or another suitable mammalian expression vector. The promoter utilized in the expression vector is chosen based on the type of cells being transfected and the desired method for regulating the level of expression. An appropriate promoter can be selected from among the promoters discussed supra. For gene therapy of heart diseases, a promoter, for example, 2MHC (see, Palermo et al., *Circ. Res.*, 78(3), 504-9 (1996)), MLC2 (see Sani, *Nature*, 314: 283-286 (1985)), CARP (see Jeyaseelan et al., *J. Biol. Chem.*, 272(36), 22800-8 (1997)), is inserted upstream of the TRAF2TD cDNA. The TRAF2TD cDNA containing expression vector is then used in a liposome-mediated transfection utilizing lipofectamine (BRL, Gibco) reagent using the supplied protocol. For transfection protocols using viral transduction, the second stage of the ex vivo treatment protocol utilizes a recombinant adenovirus vector system. In this protocol, the TRAF2TD cDNA is cloned into an adenovirus expression vector, for example, adeno-quest pQBI-AdBN/NB (QUANTUM Biotechnologies Inc.). The adenoviral transfer vector now containing the TRAF2TD cDNA is then co-transfected with adenovirus viral DNA into 293 cells. Following plaque purification and positive clone selection, recombinant adenovirus containing the TRAF2TD cDNA is amplified and then purified using conventional CsCl step gradient purification, followed by dialysis using an appropriate buffer, for example, phosphate buffered saline. The recombinant adenovirus is then used to transfect the target cells ex vivo.

Recombinant viruses according to the invention are formulated and administered in the form of doses of between about $10^4$ and about $10^{14}$ pfu. In the case of AAVs and adenoviruses, doses of from about $10^6$ to about $10^{11}$ pfu are preferably used. The term "pfu" ("plaque-forming unit") corresponds to the infective power of a suspension of virions and is determined by infecting an appropriate cell culture and measuring the number of plaques formed. The techniques for determining the pfu titre of a viral solution are well documented in the prior art.

In the third stage, the transfected cells obtained by either lipofection or recombinant adenovirus infection are grown up in culture, selecting for those cells which have been transfected. Selection can be done in a variety of ways, including using a drug marker that provides for survival and growth of only those cells which have taken up the expression vector.

In the fourth stage, the transfected cells are infused or transplanted directly into the patient, either near the tissue to be treated or at a location that allows the TRAF2TD cDNA product to be released into the circulation so as to interact with the cells subject to activation by TNF α binding. Delivery means include, but are not limited to, direct injection, or delivery by catheter, infusion pump or stent.

Example 6

In Vivo Treatment Methods

Methods of in vivo treatment can utilize a variety of different viral vectors, including adenovirus vectors, adeno-associated virus vectors, and retrovirus vectors. In a preferred in vivo treatment method of the present invention, an adenovirus system is used to introduce the TRAF2TR or TRAF2T6-cDNA into host cells. Given the relatively greater ability of the TRAF2TD cDNA to inhibit TNF α binding activation, it is preferable to use the TRAF2TD cDNA in the adenovirus expression vector. In this method, the TRAF2TD cDNA is cloned into an adenovirus transfer vector, for example, the adeno-Quest pQBI-AdBN/NB (QUANTUM Biotechnologies Inc.) or another adenovirus vector from those described supra. The promoter utilized in the expression vector is chosen based on the type of cells being transfected and the desired method for regulating the level of expression. An appropriate promoter can be selected from among the promoters discussed supra.

The adenoviral transfer vector containing the desired promoter and the TRAF2TD cDNA would be then co-transfected with adenovirus viral DNA into 293 cells. Following plaque purification and positive-clone selection, recombinant adenovirus containing the TRAF2TD cDNA is amplified and then purified using conventional CsCl step gradient purification, followed by dialysis using an appropriate buffer, for example, phosphate buffered saline.

Prior to transfecting cells in vivo, viral particle titer is determined and experiments in vitro are performed to determine the level of protein expression and the tissue culture infectious dose (TCID50). Recombinant-viruses according to the invention are formulated and administered in the form of doses of between about $10^4$ and about $10^{14}$ pfu. In the case of AAVs and adenoviruses, doses of from about $10^6$ to about $10^{11}$ pfu are preferably used. The term "pfu" ("plaque-forming unit") corresponds to the infective power of a suspension of virions and is determined by infecting an appropriate cell culture and measuring the number of plaques formed. The techniques for determining the pfu titre of a viral solution are well documented in the prior art.

The recombinant adenovirus would then be used to infect the patient at a dose of between about $10^6$ to about $10^{11}$ pfu. The recombinant adenovirus may be introduced by inhalation, by infusion, by surgical implantation, by direct injection or delivery by catheter, infusion pump or stent.

We claim:

1. An isolated nucleic acid encoding a polypeptide comprising the amino acid sequence of SEQ ID NO: 4.

2. The nucleic acid of claim 1 wherein said nucleic acid is a cDNA.

3. An isolated vector comprising the nucleic acid of claim 1.

4. An isolated cell comprising the nucleic acid of claim 1.

\* \* \* \* \*

SEQUENCE LISTING

<160> NUMBER OF SEQ ID NOS: 5

<210> SEQ ID NO 1
<211> LENGTH: 1269
<212> TYPE: DNA
<213> ORGANISM: Homo sapiens

<400> SEQUENCE: 1

```
atggctgcag ctagcgtgac cccccctggc tccctggagt tgctacagcc cggcttctcc      60
aagaccctcc tggggaccaa gctggaagcc aagtacctgt gctccgcctg cagaaacgtc     120
ctccgcaggc ccttccaggc cagtgtggc caccggtact gctccttctg cctggccagc     180
atcctcagct ctgggcctca gaactgtgct gcctgtgttc acgagggcat atatgaagaa     240
ggcatttcta ttttagaaag cagttcggcc ttcccagata tgctgcccg cagggaggtg     300
gagagcctgc cggccgtctg tcccagtgat ggatgcacct ggaaggggac cctgaaagaa     360
tacgagtttc aggaccacgt caagacttgt ggcaagtgtc gagtcccttg cagattccac     420
gccatcggct gcctcgagac ggtagagggt gagaaacagc aggagcacga ggtgcagtgg     480
ctgcgggagc acctggccat gctactgagc tcggtgctgg aggcaaagcc cctcttggga     540
gaccagagcc acgcggggtc agagctcctg cagaggtgcg agagcctgga agaagacg      600
gccacttttg agaacattgt ctgcgtcctg aaccgggagg tggagagggt ggccatgact     660
gccgaggcct gcagccggca gcaccggctg gaccaagaca agattgaagc cctgagtagc     720
aaggtgcagc agctggagag gagcattggc ctcaaggacc tggcgatggc tgacttggag     780
cagaaggtct tggagatgga ggcatccacc tacgatgggg tcttcatctg gaagatctca     840
gacttcgcca ggaagctcca ggaagctgtg gctggccgca tacccgccat cttctcccca     900
gccttctaca ccagcaggta cggctacaag atgtgtctgc gtatctacct gaacggcgac     960
ggcaccgggc gaggaacaca cctgtccctc ttctttgtgg tgatgaaggg cccgaatgac    1020
gccctgctgc ggtggccctt caaccagaag gtgaccttaa tgctgctcga ccagaataac    1080
cgggagcacg tgattgacgc cttcaggccc gacgtgactt catcctcttt tcagaggcca    1140
gtcaacgaca tgaacatcgc aagcggctgc ccctcttct gccccgtctc caagatggag    1200
gcaaagaatt cctacgtgcg ggacgatgcc atcttcatca aggccattgt ggaccctgaca    1260
gggctctaa                                                           1269
```

<210> SEQ ID NO 2
<211> LENGTH: 422
<212> TYPE: PRT
<213> ORGANISM: Homo sapiens

<400> SEQUENCE: 2

```
Met Ala Ala Ala Ser Val Thr Pro Pro Gly Ser Leu Glu Leu Leu Gln
  1               5                  10                  15

Pro Gly Phe Ser Lys Thr Leu Leu Gly Thr Lys Leu Glu Ala Lys Tyr
                 20                  25                  30

Leu Cys Ser Ala Cys Arg Asn Val Leu Arg Arg Pro Phe Gln Ala Gln
             35                  40                  45

Cys Gly His Arg Tyr Cys Ser Phe Cys Leu Ala Ser Ile Leu Ser Ser
         50                  55                  60

Gly Pro Gln Asn Cys Ala Ala Cys Val His Glu Gly Ile Tyr Glu Glu
 65                  70                  75                  80
```

```
Gly Ile Ser Ile Leu Glu Ser Ser Ala Phe Pro Asp Asn Ala Ala
                 85                  90                  95

Arg Arg Glu Val Glu Ser Leu Pro Ala Val Cys Pro Ser Asp Gly Cys
            100                 105                 110

Thr Trp Lys Gly Thr Leu Lys Glu Tyr Glu Phe Gln Asp His Val Lys
        115                 120                 125

Thr Cys Gly Lys Cys Arg Val Pro Cys Arg Phe His Ala Ile Gly Cys
    130                 135                 140

Leu Glu Thr Val Glu Gly Lys Gln Gln Glu His Glu Val Gln Trp
145                 150                 155                 160

Leu Arg Glu His Leu Ala Met Leu Leu Ser Val Leu Glu Ala Lys
                165                 170                 175

Pro Leu Leu Gly Asp Gln Ser His Ala Gly Ser Glu Leu Leu Gln Arg
            180                 185                 190

Cys Glu Ser Leu Glu Lys Lys Thr Ala Thr Phe Glu Asn Ile Val Cys
        195                 200                 205

Val Leu Asn Arg Glu Val Glu Arg Val Ala Met Thr Ala Glu Ala Cys
    210                 215                 220

Ser Arg Gln His Arg Leu Asp Gln Asp Lys Ile Glu Ala Leu Ser Ser
225                 230                 235                 240

Lys Val Gln Gln Leu Glu Arg Ser Ile Gly Leu Lys Asp Leu Ala Met
                245                 250                 255

Ala Asp Leu Glu Gln Lys Val Leu Glu Met Glu Ala Ser Thr Tyr Asp
            260                 265                 270

Gly Val Phe Ile Trp Lys Ile Ser Asp Phe Ala Arg Lys Leu Gln Glu
        275                 280                 285

Ala Val Ala Gly Arg Ile Pro Ala Ile Phe Ser Pro Ala Phe Tyr Thr
    290                 295                 300

Ser Arg Tyr Gly Tyr Lys Met Cys Leu Arg Ile Tyr Leu Asn Gly Asp
305                 310                 315                 320

Gly Thr Gly Arg Gly Thr His Leu Ser Leu Phe Phe Val Val Met Lys
                325                 330                 335

Gly Pro Asn Asp Ala Leu Leu Arg Trp Pro Phe Asn Gln Lys Val Thr
            340                 345                 350

Leu Met Leu Leu Asp Gln Asn Asn Arg Glu His Val Ile Asp Ala Phe
        355                 360                 365

Arg Pro Asp Val Thr Ser Ser Ser Phe Gln Arg Pro Val Asn Asp Met
    370                 375                 380

Asn Ile Ala Ser Gly Cys Pro Leu Phe Cys Pro Val Ser Lys Met Glu
385                 390                 395                 400

Ala Lys Asn Ser Tyr Val Arg Asp Asp Ala Ile Phe Ile Lys Ala Ile
                405                 410                 415

Val Asp Leu Thr Gly Leu
            420

<210> SEQ ID NO 3
<211> LENGTH: 1011
<212> TYPE: DNA
<213> ORGANISM: Homo sapiens

<400> SEQUENCE: 3
atgagttcgg ccttcccaga taatgctgcc cgcagggagg tggagagcct gccggccgtc      60
tgtcccagtg atgatgcac ctggaagggg accctgaaag aatacgagtt tcaggaccac     120
gtcaagactt gtggcaagtg tcgagtccct tgcagattcc acgccatcgg ctgcctcgag     180
```

```
acggtagagg gtgagaaaca gcaggagcac gaggtgcagt ggctgcggga gcacctggcc    240
atgctactga gctcggtgct ggaggcaaag cccctcttgg agaccagag ccacgcgggg     300 tcagagctcc tgcagaggtg cgagagcctg gagaagaaga cggccacttt tgagaacatt    360
gtctgcgtcc tgaaccggga ggtggagagg gtggccatga ctgccgaggc ctgcagccgg    420
cagcaccggc tggaccaaga caagattgaa gccctgagta gcaaggtgca gcagctggag    480
aggagcattg gcctcaagga cctggcgatg gctgacttgg agcagaaggt cttggagatg    540
gaggcatcca cctacgatgg ggtcttcatc tggaagatct cagacttcgc caggaagctc    600
caggaagctg tggctggccg catacccgcc atcttctccc agccttcta caccagcagg    660 tacggctaca gatgtgtct gcgtatctac ctgaacggcg acggcaccgg gcgaggaaca    720
cacctgtccc tcttctttgt ggtgatgaag ggcccgaatg acgccctgct gcggtggccc    780
ttcaaccaga aggtgacctt aatgctgctc gaccagaata accgggagca cgtgattgac    840
gccttcaggc ccgacgtgac ttcatcctct tttcagaggc cagtcaacga catgaacatc    900
gcaagcggct gccccctctt ctgccccgtc tccaagatgg aggcaaagaa ttcctacgtg    960
cgggacgatg ccatcttcat caaggccatt gtggacctga cagggctcta a            1011
```

<210> SEQ ID NO 4
<211> LENGTH: 336
<212> TYPE: PRT
<213> ORGANISM: Homo sapiens

<400> SEQUENCE: 4

```
Met Ser Ser Ala Phe Pro Asp Asn Ala Ala Arg Arg Glu Val Glu Ser
  1               5                  10                  15

Leu Pro Ala Val Cys Pro Ser Asp Gly Cys Thr Trp Lys Gly Thr Leu
             20                  25                  30

Lys Glu Tyr Glu Phe Gln Asp His Val Lys Thr Cys Gly Lys Cys Arg
         35                  40                  45

Val Pro Cys Arg Phe His Ala Ile Gly Cys Leu Glu Thr Val Glu Gly
     50                  55                  60

Glu Lys Gln Gln Glu His Glu Val Gln Trp Leu Arg Glu His Leu Ala
 65                  70                  75                  80

Met Leu Leu Ser Ser Val Leu Glu Ala Lys Pro Leu Leu Gly Asp Gln
                 85                  90                  95

Ser His Ala Gly Ser Glu Leu Leu Gln Arg Cys Glu Ser Leu Glu Lys
            100                 105                 110

Lys Thr Ala Thr Phe Glu Asn Ile Val Cys Val Leu Asn Arg Glu Val
        115                 120                 125

Glu Arg Val Ala Met Thr Ala Glu Ala Cys Ser Arg Gln His Arg Leu
    130                 135                 140

Asp Gln Asp Lys Ile Glu Ala Leu Ser Ser Lys Val Gln Gln Leu Glu
145                 150                 155                 160

Arg Ser Ile Gly Leu Lys Asp Leu Ala Met Ala Asp Leu Glu Gln Lys
                165                 170                 175

Val Leu Glu Met Glu Ala Ser Thr Tyr Asp Gly Val Phe Ile Trp Lys
            180                 185                 190

Ile Ser Asp Phe Ala Arg Lys Leu Gln Glu Ala Val Ala Gly Arg Ile
        195                 200                 205

Pro Ala Ile Phe Ser Pro Ala Phe Tyr Thr Ser Arg Tyr Gly Tyr Lys
    210                 215                 220
```

```
            Met Cys Leu Arg Ile Tyr Leu Asn Gly Asp Gly Thr Gly Arg Gly Thr
            225                 230                 235                 240

His Leu Ser Leu Phe Phe Val Val Met Lys Gly Pro Asn Asp Ala Leu
                            245                 250                 255

Leu Arg Trp Pro Phe Asn Gln Lys Val Thr Leu Met Leu Leu Asp Gln
                        260                 265                 270

Asn Asn Arg Glu His Val Ile Asp Ala Phe Arg Pro Asp Val Thr Ser
                        275                 280                 285

Ser Ser Phe Gln Arg Pro Val Asn Asp Met Asn Ile Ala Ser Gly Cys
                        290                 295                 300

Pro Leu Phe Cys Pro Val Ser Lys Met Glu Ala Lys Asn Ser Tyr Val
            305                 310                 315                 320

Arg Asp Asp Ala Ile Phe Ile Lys Ala Ile Val Asp Leu Thr Gly Leu
                            325                 330                 335

<210> SEQ ID NO 5
<211> LENGTH: 2262
<212> TYPE: DNA
<213> ORGANISM: Homo sapiens
<220> FEATURE:
<221> NAME/KEY: misc_feature
<222> LOCATION: ()..()
<223> OTHER INFORMATION: TRAF2 truncated sequence contains an internal
      deletion of base pairs 421 to 657

<400> SEQUENCE: 5
gaattccggc gcgctgcgac cgttggggct ttgttcgcgg gggtcacagc tctcatggct      60
gcagctagcg tgaccccccc tggctccctg gagttgctac agcccggctt ctccaagacc     120
ctcctgggga ccaagctgga agccaagtac ctgtgctccg cctgcagaaa cgtcctccgc     180
aggcccttcc aggcgcagtg tggccaccgg tactgctcct tctgcctggc cagcatcctc     240
agctctgggc tcagaactg tgctgcctgt gttcacgagg catatatga agaaggcatt      300 tctattttag aaagcagttc ggccttccca gataatgctg cccgcaggga ggtggagagc     360
ctgccggccg tctgtcccag tgatggatgc acctggaagg ggaccctgaa agaatacgag     420
agctgccacg aaggccgctg cccgctcatg ctgaccgaat gtcccgcgtg taaaggcctg     480
gtccgccttg gtgaaaagga cgccaccctg agcacgagt gccccgagag aagcctgagc     540
tgccggcatt gccgggcacc ctgctgcgga gcagacgtga aggcgcacca cgaggtctgc     600
cccaagttcc ccttaacttg tgacggctgc ggcaagaaga gatccccg ggagaagttt      660 caggaccacg tcaagacttg tggcaagtgt cgagtccctt gcagattcca cgccatcggc     720
tgcctcgaga cggtagaggg tgagaaacag caggagcacg aggtgcagtg gctgcgggag     780
cacctggcca tgctactgag ctcggtgctg gaggcaaagc ccctcttggg agaccagagc     840
cacgcggggt cagagctcct gcagaggtgc gagagcctgg agaagaagac ggccactttt     900
gagaacattg tctgcgtcct gaaccgggag gtggagaggg tggccatgac tgccgaggcc     960
tgcagccggc agcaccggct ggaccaagac aagattgaag ccctgagtag caaggtgcag    1020
cagctggaga ggagcattgg cctcaaggac ctggcgatgg ctgacttgga gcagaaggtc    1080 aggccccttcc aggcgcagtg tggccaccgg tactgctcct tctgcctggc cagcatcctc    1140
aggaagctcc aggaagctgt ggctggccgc ataccgcca tcttctcccc agccttctac    1200
accagcaggt acggctacaa gatgtgtctg cgtatctacc tgaacggcga cggcaccggg    1260
cgaggaacac acctgtccct cttctttgtg gtgatgaagg gcccgaatga cgccctgctg    1320
cggtggccct tcaaccagaa ggtgacctta atgctgctcg accagaataa ccgggagcac    1380
```

```
gtgattgacg ccttcaggcc cgacgtgact tcatcctctt ttcagaggcc agtcaacgac    1440
atgaacatcg caagcggctg cccctcttc tgccccgtct ccaagatgga ggcaaagaat    1500
tcctacgtgc gggacgatgc catcttcatc aaggccattg tggacctgac agggctctaa   1560
ctgcccccta ctggtgtctg ggggttgggg gcagccaggc acagccggct cacggagggg   1620
ccaccacgct gggccagggt ctcactgtac aagtgggcag gggccccgct tgggcgcttg   1680
ggagggtgtc ggcctgcagc caagttcact gtcacggggg aaggagccac cagccagtcc   1740
tcagatttca gagactgcgg aggggcttgg cagacggtct tagccaaggg ctgtggtggc   1800
attggccgag ggtcttcggg tgcttcccag cacaagctgc ccttgctgtc ctgtgcagtg   1860
aagggagagg ccctgggtgg gggacactca gagtgggagc acatcccagc agtgcccatg   1920
tagcaggagc acagtggatg gccttgtgtc cctcgggcat gacaggcaga aacgagggct   1980
gctccaggag aagggcctcc tgctggccag agcaaggaag gctgagcagc ttggttctcc   2040
cctctggccc ctggagagaa gggagcattc ctagacccct gggtgcttgt ctgcacagag   2100
ctctggtctg tgccaccttg gccaggctgg ctgtgggagg gtctggtccc acgccgcctc   2160
tgctcagaca ctgtgtggga gggcacagca cagctgcggg taaagtgtga gagcttgcca   2220
tccagctcac gaagacagag ttattaaacc attacaaatc tc                     2262
```